(12) United States Patent
McKenzie et al.

(10) Patent No.: US 7,318,924 B2
(45) Date of Patent: Jan. 15, 2008

(54) ANTIBODIES AGAINST CANCER

(75) Inventors: Ian Farquhar Campbell McKenzie, Point Lonsdale (AU); Pei-Xiang Xing, Heidelberg Heights (AU); Xiu Feng Hu, Heidelberg Heights (AU)

(73) Assignee: The Austin Research Institute, Heidelberg (AU)

( * ) Notice: Subject to any disclaimer, the term of this patent is extended or adjusted under 35 U.S.C. 154(b) by 467 days.

(21) Appl. No.: 10/470,013

(22) PCT Filed: Mar. 26, 2002

(86) PCT No.: PCT/AU02/00362

§ 371 (c)(1),
(2), (4) Date: Nov. 26, 2003

(87) PCT Pub. No.: WO02/077033

PCT Pub. Date: Oct. 3, 2002

(65) Prior Publication Data
US 2004/0176576 A1 Sep. 9, 2004

(30) Foreign Application Priority Data
Mar. 26, 2001 (AU) .................................. PR 3958

(51) Int. Cl.
*A61K 39/395* (2006.01)
(52) U.S. Cl. ................. 424/139.1; 424/130.1; 424/138.1; 424/141.1; 424/155.1; 424/156.1; 424/181.1; 424/178.1
(58) Field of Classification Search ............... None
See application file for complete search history.

(56) References Cited

U.S. PATENT DOCUMENTS

| | | |
|---|---|---|
| 5,171,665 A | 12/1992 | Hellstrom et al. |
| 5,256,643 A | 10/1993 | Persico et al. |
| 5,264,557 A | 11/1993 | Salomon et al. |
| 5,620,866 A | 4/1997 | Salomon et al. |
| 5,650,285 A | 7/1997 | Salomon et al. |
| 5,654,140 A | 8/1997 | Persico et al. |
| 5,792,616 A | 8/1998 | Persico et al. |
| 5,854,399 A | 12/1998 | Solomon et al. |
| 5,981,215 A | 11/1999 | Meissner et al. |
| 6,207,153 B1 | 3/2001 | Dan et al. |
| 6,333,410 B1 | 12/2001 | Chari et al. |
| 2003/0232755 A1 | 12/2003 | Williams et al. |
| 2004/0146940 A1 | 7/2004 | Sanicola-Nadel et al. |
| 2005/0255117 A1 | 11/2005 | Sanicola-Nadel et al. |

FOREIGN PATENT DOCUMENTS

| | | |
|---|---|---|
| WO | WO 00/06723 A1 | 2/2000 |
| WO | 0042832 A2 | 7/2000 |
| WO | WO 02/16413 A2 | 2/2002 |
| WO | WO 02/22808 A2 | 3/2002 |
| WO | WO 02/088170 A2 | 11/2002 |

OTHER PUBLICATIONS

Johnson et al Cancer Treatment Reviews vol. 2 p. 1-31 (1975).*
Weiner, Seminars in Oncology vol. 26 p. 41-50 (1999).*
Fundamental Immunology, 4th edition, ed. William Paul, pp. 58-59, 91-94 and 106-108) (1998).*
Ciardiello, Fortunato et al., "Cooperative Inhibition of Renal Cancer Growth by Anti-Epidermal Growth Factor Receptor Antibody and Protein Kinase A Antisense Oligonucleotide," *Journal of the National Cancer Institute*, Jul. 15, 1998, pp. 1087-1094, vol. 90, No. 14.
Ciardiello, Fortunato et al., "Inhibition of CRIPTO expression and tumorigenicityi in human colon cancer cells by antisense RNA and oligodeoxynucleotides," *Oncogene*, Jan. 1994, pp. 291-298, vol. 9. Macmillan Press Ltd.
Nakamura, Kazuyasu et al., "Apoptosis induction of human lung cancer cell line in multicellular heterospheroids with humanized antiganglioside GM2 monoclonal antibody," *Cancer Research*, Oct. 15, 1999, pp. 5323-5330, vol. 59, No. 20. (ABSTRACT).
Normanno et al., "Synergistic growth inhibition and induction of apoptosis by a novel mixed backbone antisense oligonucleotide targeting CRIPTO in combination with C225 anti-EGFR monoclonal antibody and 8-Cl-cAMP in human GEO colon cancer cells," *Oncology Reports*, 1999, pp. 1105-1109, vol. 6.
Brandt et al., "Identification and Biological Characterization of an Epidermal Growth Factor-related Protein: Cripto-1," *The Journal of Biological Chemistry*, Jun. 24, 1994, pp. 17320-17328, vol. 269.
Bianco et al., "Cripto-1 Indirectly Stimulates the Tyrosine Phosphorylation of *erb* B-4 through a Novel Receptor," *The Journal of Biological Chemistry*, Mar. 26, 1999, pp. 8624-8629, vol. 274.
New et al., "Identification of Basic Fibroblast Growth Factor Sènsitivity and Receptor and Ligand Expression in Human Colon Tumor Cell Lines," *Journal of Cellular Physiology*, 1992, pp. 320-326, vol. 150.
Sandler et al., "Expression of p53 protein in rat colon cancer cell lines transfected with *Rous sarcoma* virus-33," *Cancer Letters*, 1997, pp. 133-137, vol. 121.
Freidmann et al., "Characterization of the Proto-oncogene Pim-1; Kinase Activity and Substrate Recognition Sequence," *Archives of Biochemistry and Biophysics*, Nov. 1, 1992, pp. 594-601, vol. 298.

(Continued)

*Primary Examiner*—Sheela J. Huff
(74) *Attorney, Agent, or Firm*—Rothwell, Figg, Ernst & Manbeck

(57) ABSTRACT

An isolated binding partner of a Cripto-1 protein, Pim-1 protein or an antigen present in a colon cancer cell lysate is described. The binding partner inhibits growth of one or more cancer cell types and may be used in an anti-cancer agent for treating cancer in a subject. The binding partner may also be used in a method of inducing apoptosis in a cancer cell, as well as in a method of sensitizing a cancer cell to a cytotoxic compound. In addition, a cancer vaccine is described wherein the vaccine comprises a Cripto-1 protein (or an antigenic fragment thereof), Pim-1 protein (or an antigenic fragment thereof) or an antigen present in a colon cancer cell lysate or, alternatively, comprises an expressible DNA molecule encoding a Cripto-1 protein (or an antigenic fragment thereof), Pim-1 protein (or an antigenic fragment thereof) or an antigen present in a colon cancer cell lysate.

17 Claims, 17 Drawing Sheets

OTHER PUBLICATIONS

Figure 1:
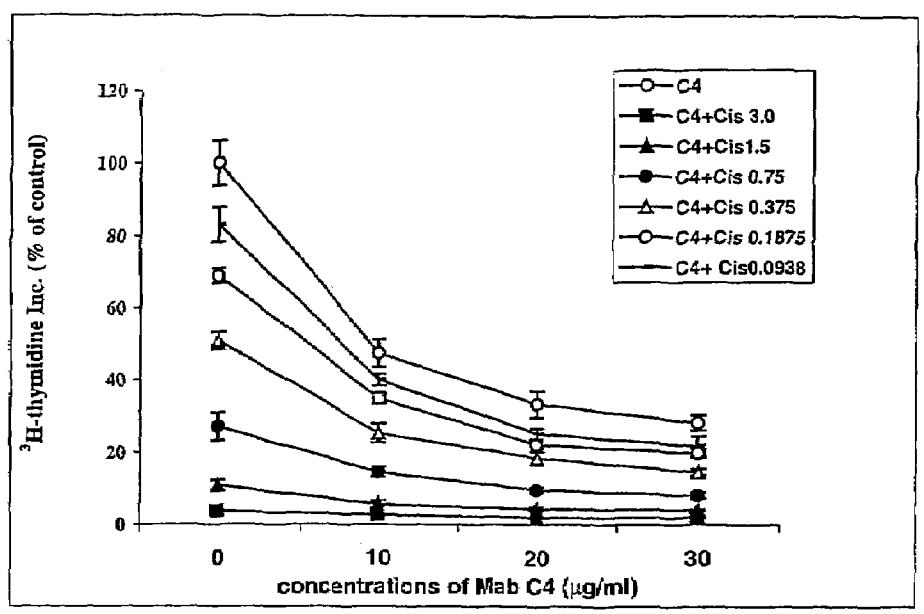

Adkins, Heather B., et al., "Antibody blockade of the Cripto CFC domain suppresses tumor cell growth in vivo," The Journal of Clinical Investigation, 112(4):575-587 (Aug. 2003).

Berzofsky, Jay A., et al., "Immunogenicity and Antigen Structure," Fundamental Immunology, Third Edition, William E. Paul, ed., Raven Press, Ltd., New York, NY (1993), Chapter 8, pp. 235-282.

Campbell, Alisa M., "Monoclonal Antibody Technology: The Production and Characterization of Rodent and Human Hybridomas," in Laboratory Techniques in Biochemistry and Molecular Biology, R.H. Burden et al., eds., vol. 13, pp. 1-32 (1984).

Hu, Xiu Feng, et al., "Cripto Monoclonal Antibodies," Drug News Perspect, 18(5):293-303 (Jun. 2005).

Panico, Luigi, et al., "Differential Immunohistochemical Detection of Transforming Growth Factor α, Amphiregulin and Cripto in Human Normal and Malignant Breast Tissues," Int. J. Cancer, 65:51-56 (1996).

Qi, C.-F., et al., "Expression of transforming growth factor α, amphiregulin and cripto-1 in human breast carcinomas," Br. J. Cancer, 69:903-910 (1994).

Schlom, Jeffrey, et al., "Monoclonal Antibodies: They're More and Less Than You Think," Molecular and Cellular Research for Future Diagnosis and Therapy, Broder (ed.), pp. 95-134, 1991.

Paul, William E., ed., Fundamental Immunology, 4th Ed., pp. 58-59, 91-94, 106-108 (1998). Lippincott-Raven Publishers, Philadelphia, Pennsylvania.

* cited by examiner

Days post tumour cell cell inoculation

Du145 cells (5x10$^4$) cells were seeded in 25cm$^2$ flasks in 10 ml of medium in the presence and absence of 50μg/ml of mAb C3. Viable cells were counted by using a phase-contrast microscope. Points mean of triplicate experiments, bars, SD.

Inhibition effect by cross-linking C3

Fig.4. Percentage of change in thymidine incorporation of MCF7, LS174T cells as a function in the presence of anti-colon cancer mAbs 1.14, 1.68, 2.20, 3.60 for 72 hours compared to mAb BCP7 (anti-muc1).

ANTIBODIES AGAINST CANCER

FIELD OF THE INVENTION

The present invention relates to anti-cancer agents and especially agents which inhibit the in vitro and in vivo growth of human colon, prostate and breast cancer cells. The present invention also relates to cancer vaccines.

BACKGROUND TO THE INVENTION

In the early 1980's, there was considerable interest in the development of monoclonal antibodies (Mabs) for use as anti-cancer agents. In some cases, these were designed to be "magic bullets" delivering, by way of conjugation, various cytotoxic compounds (eg toxins) or other substances (eg isotopes and drugs) to the cancerous cells. However, due to a number of reasons including poor specificity, poor penetration (ie with solid tumours) and the induced HAMA (ie human anti-mouse antibody) response, these Mab-based anti-cancer agents were unsuccessful and largely abandoned.

In recent times, there has been renewed interest in Mab-based anti-cancer agents and many of the problems previously experienced have been addressed by genetic engineering techniques (Hudson P. J., "Recombinant-antibody constructs in cancer therapy", Curr Opin Immunol, 11, pp 548-557 (1999); the disclosure of which is to be considered as incorporated herein by reference). Indeed, there are currently three Mabs (ie the humanised HER2/neuMab marketed under the name Transtuzumab for treatment of HER2/neu positive breast cancer, humanised anti-CD20 Mab known as Rituxan for treatment of Non-Hodgkin lymphoma, and C225 which is an anti-EGFR Mab) which are either being used or are in clinical trials. These antibodies do not act primarily as cytotoxic antibodies nor by Fc mediated inflammatory responses, but rather bind antigen leading to interference in cell signaling and apoptosis. For example, in the case of the HER2/neu Mab, the antibody prevents or "blocks" the binding of a growth factor resulting in the death of HER2/neu positive breast cancer cells.

There is a clear need for more anti-cancer agents to complement existing treatments of cancers. By immunising rats with or an antigenic portion of a Cripto-1 protein (Montuori N, et al. "isolation and characterisation of the CRIPTO autosomal gene and its X-linked related sequence", Am J Hum Genet, 49(3), pp 555-565 (1991)) known to be expressed in certain cancer cells, or a fusion protein of a Pim-1 protein (Friedmann M, et al. "Characterisation of the proto-oncogene pim-1: kinase activity and substrate recognition sequence", Arch Biochem Biophys, 298 (2), pp 594-601 (1992), or a colon cancer cell lysate, the present applicant has produced monoclonal antibodies which have been found, surprisingly, to inhibit growth of various cancer cell lines.

SUMMARY OF THE INVENTION

In a first aspect, the present invention provides an isolated binding partner of a Cripto-1 protein, Pim-1 protein or an antigen present in a colon cancer cell lysate, wherein said binding partner inhibits growth of one or more cancer cell types.

In a second aspect, the present invention provides an anti-cancer agent comprising a binding partner of a Cripto-1 protein, Pim-1 protein or an antigen present in a colon cancer cell lysate, wherein said binding partner inhibits growth of one or more cancer cell types.

In a third aspect, the present invention provides a method of treating cancer in a subject, said method comprising administering to said subject an effective amount of an anti-cancer agent according to the second aspect.

In a fourth aspect, the present invention provides a cancer vaccine comprising a Cripto-1 protein, Pim-1 protein or an antigen present in a colon cancer cell lysate or, alternatively, an expressible DNA molecule encoding a Cripto-1 protein, Pim-1 protein or an antigen present in a colon cancer cell lysate.

In a fifth aspect, the present invention provides a method of treating cancer in a subject, said method comprising administering to said subject an effective amount of a cancer vaccine according to the fourth aspect.

In a sixth aspect, the present invention provides a method for inducing apoptosis in a cancer cell, said method comprising treating said cell with a binding partner of a Cripto-1 protein, Pim-1 protein or an antigen present in a colon cancer cell lysate.

In a seventh aspect, the present invention provides a method of sensitising a cancer cell to a cytotoxic compound, said method comprising treating said cell with a binding partner of a Cripto-1 protein, Pim-1 protein or an antigen present in a colon cancer cell lysate.

DETAILED DESCRIPTION OF THE INVENTION

The binding partner of the present invention preferably inhibits growth of one or more of colon cancer cells, breast cancer cells, prostate cancer cells, leukemia cells and lung cancer cells, and is characterised in that it binds to Cripto-1 protein, Pim-1 protein or an antigen present in a colon cancer cell lysate.

Preferably, the binding partner is an antibody or fragment thereof, but might also be a receptor protein for the Cripto-1 protein (Bianco C. et al., "Cripto-1 indirectly stimulates the tyrosine phosphorylation of erb B-4 through a novel receptor", J Biol Chem, 274(13), pp 8624-8629 (1999)), Pim-1 protein or colon cell lysate antigen or, otherwise, any other peptide, polypeptide or protein which specifically binds to the Cripto-1 protein, Pim-1 protein or colon cell lysate antigen. The term "specifically binds" in this context, is to be understood to refer to binding characteristics of a peptide, polypeptide or protein which binds exclusively to the Cripto-1 protein, Pim-1 protein or colon cell lysate antigen or with only negligible cross reaction with other mammalian proteins.

More preferably, the binding partner is a monoclonal antibody or fragment thereof and, particularly, is selected from monoclonal antibodies or fragments thereof which bind to an antigenic determinant of Cripto-1 protein comprising an amino acid sequence substantially corresponding to the amino acid sequence;

CPPSFYGRNCEHDVRKE,　　(SEQ ID NO: 1)

and/or an antigen present in a colon cancer cell lysate, wherein said antigen has a molecular weight of 16 Kd or 30 Kd as estimated by SDS-PAGE. The 16 Kd and/or 30 Kd antigen may be a growth factor required for growth of colon cancer cells and/or breast cancer cells.

Monoclonal antibodies according to the present invention may be produced by any of the standard techniques in the art Fragments of monoclonal antibodies such as F(ab')$_v$, Fab and Fc may be produced by, for example, pepsin and papain cleavage as is standard in the art or by recombinant DNA techniques involving expression of antibody genes isolated from a hybridoma cell line or antibody-producing animal cell. Particularly preferred antibody fragments are single chain Fv (scfv) antibody fragments. Methods for producing scFvs are described in Pluckthun A, Bio/Technology, 9, pp 545-551(1991) and U.S. Pat. No. 4,946,778. It is to be understood that the disclosures contained within these two references are incorporated herein by reference.

It is believed that antibody fragments according to the invention may provide advantages over monoclonal antibodies and other "large" binding partner types since they may exhibit improved penetration of solid tumours, particularly large tumours.

Monoclonal antibodies and antibody fragment according to the present invention may be humanised in accordance with the technique described in U.S. Pat. No. 5,225,539 (the disclosure of which is incorporated herein by reference).

Monoclonal antibodies and antibody fragments may also be produced by using spleen cells from an immunised animal (eg mouse or rat) fused to a human myeloma line (eg Karpas 707 H human myeloma cell line; Karpas A, et al. "A human myeloma cell line suitable for the generation of human monoclonal antibodies", Proc Natl Acad Sci USA, 98, pp 1799-1804 (2001)), to produce human antibodies or antibody fragments. Chimeric mouse/human monoclonal antibodies may be made in accordance with Mount P. F., et al. "Chimeric (mouse/human) anti-colon cancer antibody c30.6 inhibits the growth of human colorectal cancer xenografts in scid/scid mice", Cancer Research, 54, pp 6160-6166 (1994), which is also incorporated herein by reference.

Monoclonal antibodies and antibody fragments may be produced in large amounts by standard techniques (eg in either tissue culture or serum free using a fermenter) and purified using affinity columns such as protein A (eg for murine Mabs), Protein G (eg for rat Mabs) or MEP HYPER-CEL (eg for IgM and IgG Mabs).

The binding partner of the present invention may be conjugated to a cytotoxic compound or other substances such as those mentioned above. Preferred cytotoxic compounds include first line chemotherapeutics such as anthracyclines (such as Idarubicin, Doxorubcin, Daunorubicin and Epirubicin), 5FU, topoisomerase inhibitors (such as Irinotecan), Cisplatin, Carboplatin and Taxol.

The binding partner of the present invention may also be conjugated to a first binding protein (eg biotin) to enable cross-linking between binding partners by administering a second binding protein (eg avidin) which binds with the first binding protein. In in vitro experimentation described hereinafter in Example 11, cross-linking with secondary antibodies achieves an increase in the inhibition of growth of breast cancer cells. Further preliminary experimentation has indicated that a similar result may be achieved with colon cancer cells.

Further, the binding partner of the present invention may be cross-linked to antibodies such as Panorex (Centacor, Glaxo), Rituxin (Genentech, Roche) or, Herceptin (Genentech, Roche). These second antibodies have been shown to be effective against colon cancer, lymphoma and breast cancer respectively.

Preferably, the binding partner of the present invention is combined with a suitable pharmaceutically-acceptable carrier or diluent to form an anti-cancer agent (which may be for human or animal use). Suitable carriers or diluents include isotonic saline solutions, for example, phosphate-buffered saline. The composition may be formulated for parenteral, intramuscular, intravenous, subcutaneous, intraocular, oral or transdermal administration. Typically, the binding partner (eg antibody or antibody fragment) may be administered at a dose of from about 0.01 to about 30 mg/kg body weight, preferably from 0.1 to 10 mg/kg body weight. It is to be understood, however, that the routes of administration and dosages mentioned are intended to serve only as a guide since a person skilled in the art would be able to readily determine the optimum route of administration and dosage for any particular subject and cancer condition.

The anti-cancer agent may be used in a method of treating cancer in a subject. Said method may bring about a reduction in the size of the cancer or, at least, inhibit further growth and/or spread. Said method may also be used in combination with traditional cancer treatments such as radiotherapy, chemotherapy (eg using anthracyclines, 5FU, topoisomerase inhibitors, Cisplatin and Carboplatin), or hormone therapy or therapies utilising hormone modifiers (eg Catamoxifen).

The present invention also extends to vaccines for cancer and to their use in methods of treating cancer in a subject Such vaccines may comprise a Cripto-1 protein (or an antigenic fragment thereof), Pim-1 protein (or an antigenic fragment thereof) or an antigen present in a colon cancer cell lysate or, alternatively, an expressible DNA molecule encoding a Cripto-1 protein (or an antigenic fragment thereof), Pim-1 protein (or an antigenic fragment thereof) or an antigen present in a colon cancer cell lysate.

Typically, such vaccines are prepared as injectables, either as liquid solutions or suspensions; solid forms suitable for solution in, or suspension in, liquid prior to injection may also be prepared. The preparation may also be emulsified, or the protein or DNA encapsulated in liposomes. The protein or DNA may also be mixed with excipients or adjuvants which are pharmaceutically acceptable. Suitable excipients are, for example, water, saline, dextrose, glycerol, ethanol, or the like and combinations thereof. Suitable adjuvants include aluminum hydroxide, aluminum phosphate, and aluminum potassium sulfate (alum).

The present invention further extends to a method for inducing apoptosis in a cancer cell, said method comprising treating said cell with a binding partner of a Cripto-1 protein, Pim-1 protein or an antigen present in a colon cancer cell lysate. The amount of the binding partner used to treat the cancer cell will vary depending upon the nature and identity of the particular binding partner, as well as the environment of the cancer cell (eg in an in vitro cell culture, or in an in vivo setting such as a tumour model or a cancer patient). It is however, well within the skill of persons skilled in the art to determine an effective apoptosis-inducing amount of the binding partner.

The present invention still further extends to a method of sensitising a cancer cell to a cytotoxic compound, said method comprising treating said cell with a binding partner of a Cripto-1 protein, Pim-1 protein or an antigen present in a colon cancer cell lysate. The amount of the binding partner used to sensitise the cancer cell will vary depending upon the nature and identity of the particular binding partner, as well as the environment of the cancer cell (eg in an in vitro cell culture, or in an in vivo setting such as a tumour model or a cancer patient), and the nature and identity of the cytotoxic cell to which the cell is to be sensitised. It is however, well within the skill of persons skilled in the art to determine an effective sensitising amount of the binding partner.

Finally, the present invention extends to a method of inducing a CTL response to cancer cells in a subject, said method comprising administering to said subject an effective amount of a peptide comprising an amino acid sequence substantially corresponding to:

ELNRTCCLNGGTCMLGSFCACPPSFYGPNCEHDVRKE (SEQ ID NO:2)

or an antigentic fragment thereof.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "substantially corresponding" as used in relation to an amino add sequence is intended to encompass the specified amino acid sequence as well as related amino add sequences which differ only by the inclusion of one or more amino add substitutions, insertions or additions which do not substantially alter the biological activity of the specified amino acid sequence. In particular, the term is intended to encompass related amino acid sequences which differ only by the inclusion of one or more conservative amino acid substitutions. By conservative amino acid substitutions, the intended combinations are: G, A; V, I, L, M; D, E; N, Q; S, T; K, R, H; F, Y, W, H; and P, Nα-alkylamino adds.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The invention will hereinafter be further described by way of the following non-limiting examples and accompanying figures.

BRIEF DESCRIPTION OF THE ACCOMPANYING FIGURE(S)

FIG. 1: Provides graphical results showing inhibition of LS174T colon cancer cells by Mab C4 as well as enhanced sensitivity of the cells to Cisplatin (Cis) caused by Mab C4, after 72 h incubation as measured by $^3$H-thymidine incorporation (Inc.).

Figure 2:
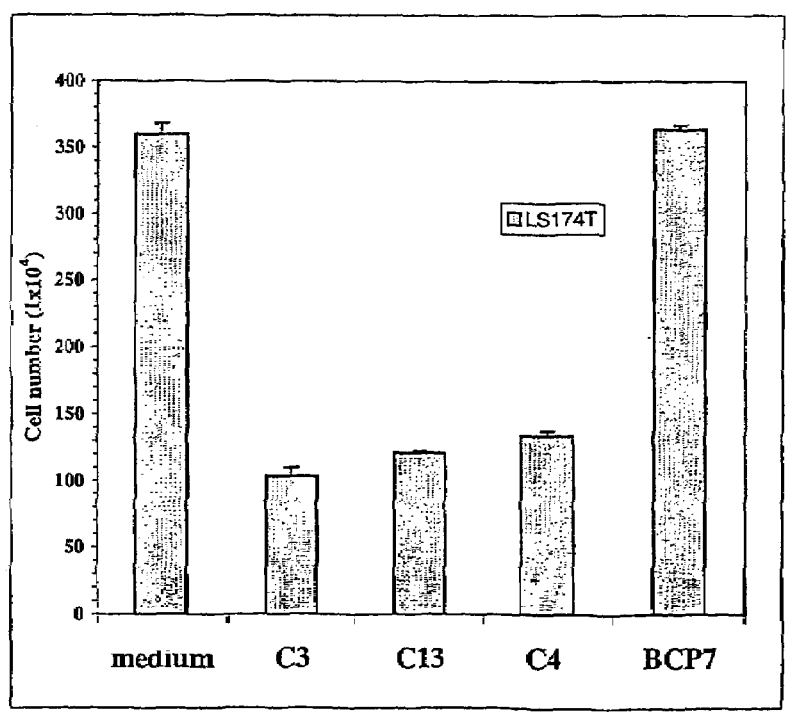

FIG. 2: Provides a bar graph of results demonstrating an inhibitory effect of Mabs C3, C4 and C13 and control Mab BCP7 (anti-mucin1 Mab) on the colon cancer cell line LS174T.

FIG. 3: Provides photographs of breast cancer tissue (A) and normal breast tissue (B) samples subjected to immunoperoxidase staining with Mab C4. No staining is seen in the normal breast tissue.

Figure 4A:
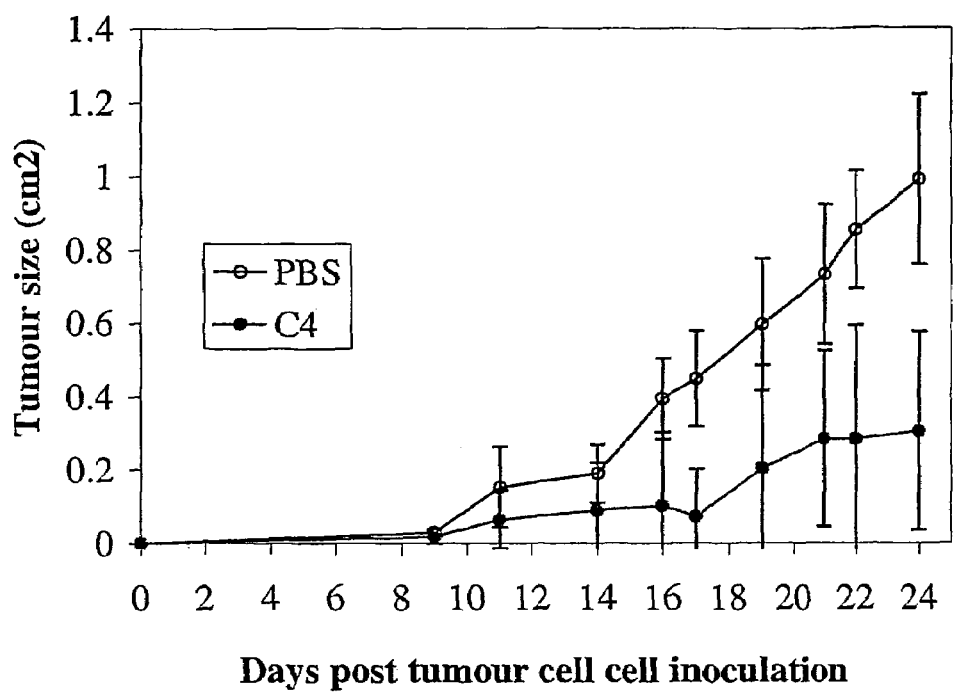

FIG. 4A: Provides graphical results showing the inhibitory effect of Mab C4 in SCID mice. SCID mice were inoculated with 2×10$^6$ of prostate cancer DU145 cells subcutaneously and treated with MabC4.

Figure 4B:
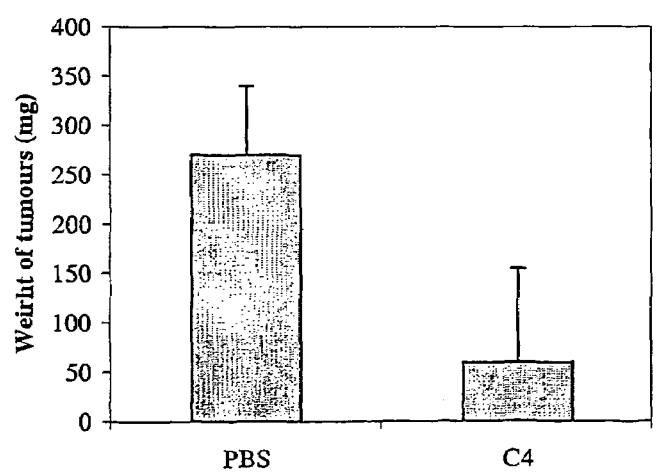

FIG. 4B: Provides results, in bar graph form, of the effect of Mab C4 on tumour size (by weight) with treated and untreated SCID mice after 24 days following innoculation of prostate cancer DU145 cells and Mab C4.

Figure 5A:
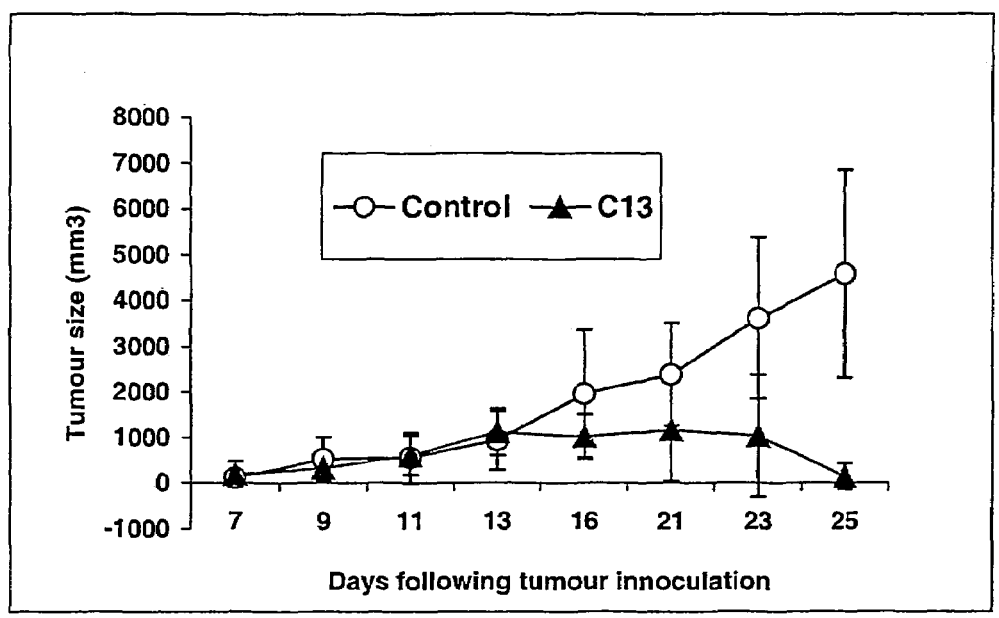

FIG. 5A: Provides graphical results showing the inhibitory effect of Mab C13 in SCID mice. SCID mice were inoculated with 2.5×10$^6$ of colon cancer Ls174T cells subcutaneously and treated with Mab C13.

Figure 5B:
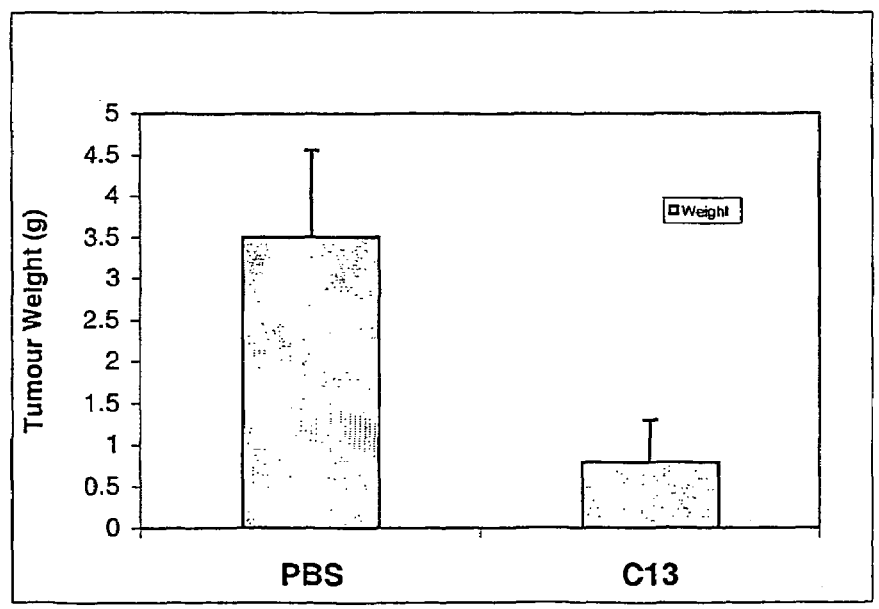

FIG. 5B: Provides results, in bar graph form, of the effect of Mab C13 on tumour size (by weight) with treated and untreated SCID mice after 25 days following innoculation of colon cancer LS174T cells and Mab C13.

Figure 6:

FIG. 6: Shows the results of DNA Fragmentation of apoptotic cells induced by the anti-Cripto-1 Mab, C3.

Figure 7:
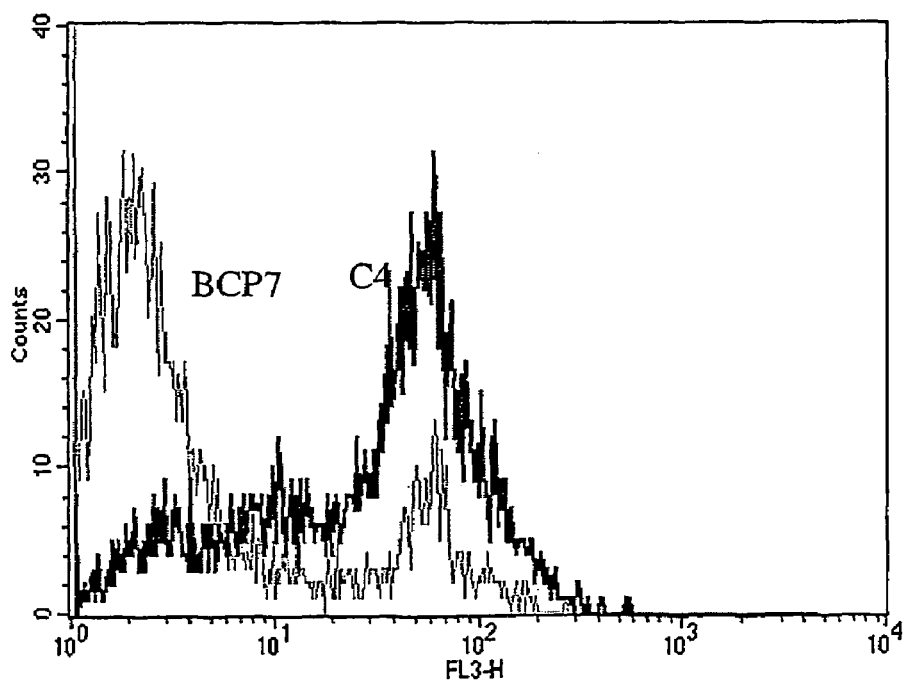

FIG. 7: Provides graphical results of FACS assays to determine propidium iodide (PI) staining, an indicator of apoptosis, in colon cancer cells LS174T treated for 72 hours with Mab C4 and the control Mab, Mab BCP7.

Figure 8:
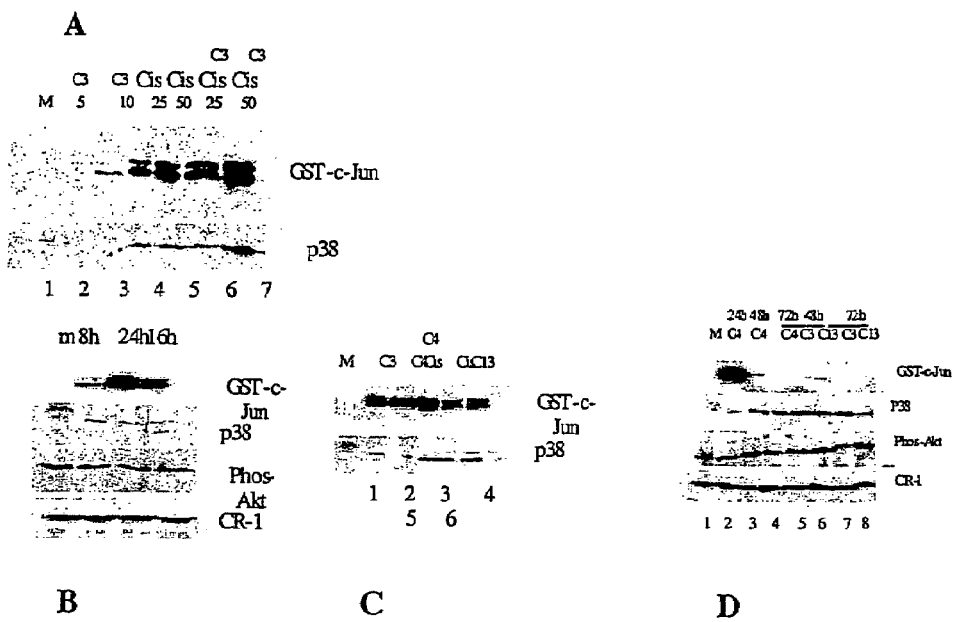

FIG. 8A: Shows the activation of JNK and p38 in LS174T cells which were treated with medium (Lane 1), with C3 (5, 10 µg/ml) (Lanes 2, 3); Cisplatin (25, 50 µg/ml) (Lanes 4, 5); and the combination of C3 (10 µg/ml) and Cisplatin (25, 50 µg/ml) (Lanes 6, 7) for 3 hours. JNK is activated in a dose dependant manner. The combination of C3 and Cisplatin (Cis) further enhanced activation of JNK. P38 was not affected by C3 but was activated by Cisplatin.

FIG. 8B: Shows the activation of JNK and p38 in LS174T cells which were incubated with medium (m), C4 at 10 µg/ml for 8, 24 or 16 hours.

FIG. 8C: Shows the activation of JNK and p38 in LS174T cells following 16 hours incubation with medium (1), C3 (10 µg/ml) (2), C4 (10 µg/ml) and Cisplatin (25 µg/ml) (4), Cisplatin (25 µg/ml) (5), and C13 (10 µg/ml) (6).

FIG. 8D: Shows the activation of JNK and p38 in the LS174T cells following incubation with medium (M), C4 (10 µg/ml) for 24 h, 48 h and 72 h (Lanes 2, 3, 4); C3 (10 µg/ml), C13 for 48 h (Lanes 5, 6) and 72 hours (lane 7, 8); C3 for 48 h (Lane 9). M, medium.

Figure 9:
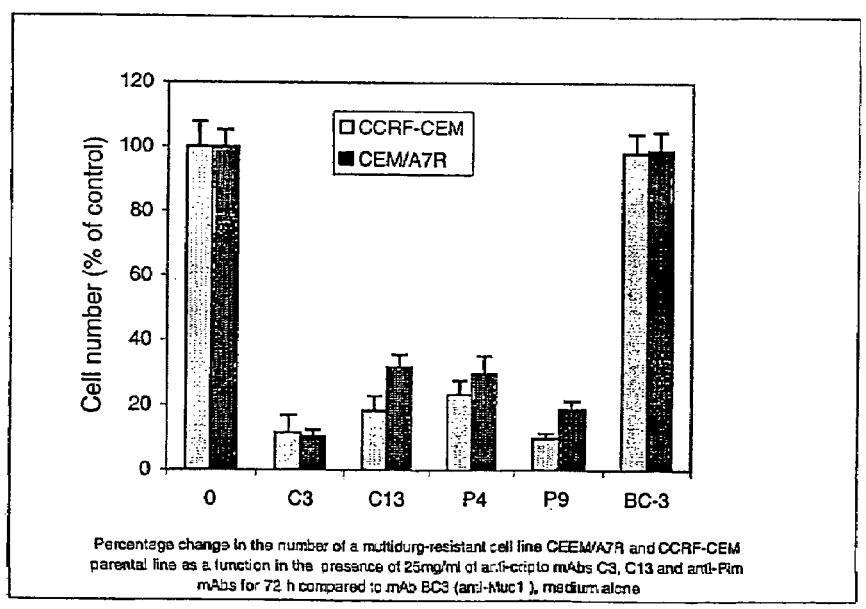

FIG. 9: Provides graphical results showing inhibition of growth of CCRF-CEM and CEM/A7R cells (Austin Research Institute, Heidelberg, Victoria, Australia) by anti-Cripto-1 Mabs (ie C3 and C13), and anti-Pim-1 Mabs (ie P4 and P9).

FIG. 10: Shows graphical results demonstrating the effects of the drug Epirubicin on 3 cell lines: leukemia cell CEM A7, the drug resistant variant CEM A7/R and mouse thyoma cells E3 (A), the effect of Mab C4 on drug resistant leukaemia cell line CEM/A7R (B) and mouse thyoma cells E3 (C) treated with Epirubicin.

Figure 11:
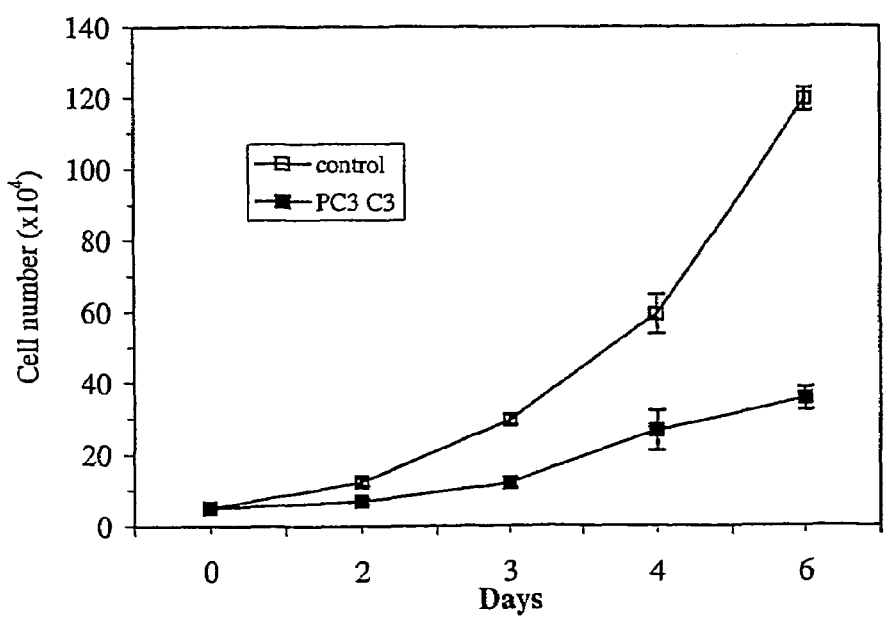

FIG. 11: Provides graphical results showing inhibition of prostate cancer cell PC3 growth by Mab C3

Figure 12:
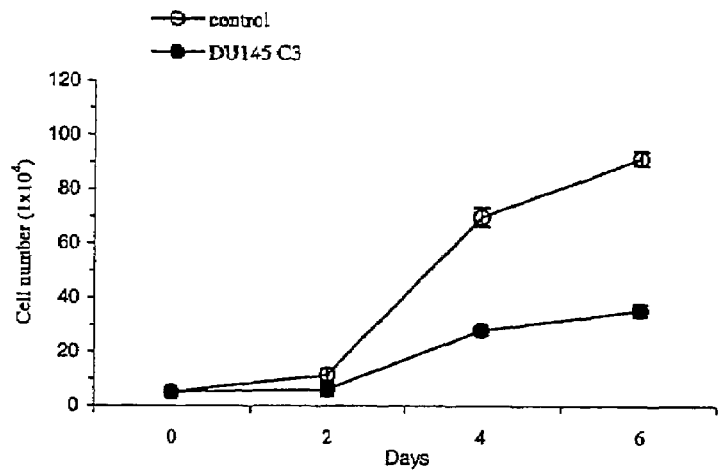

FIG. 12: Provides tabled and graphical results which show inhibition of growth of prostate cancer cell line DU 145 by the anti-Cripto-1 Mab C3, over time.

Figure 13:
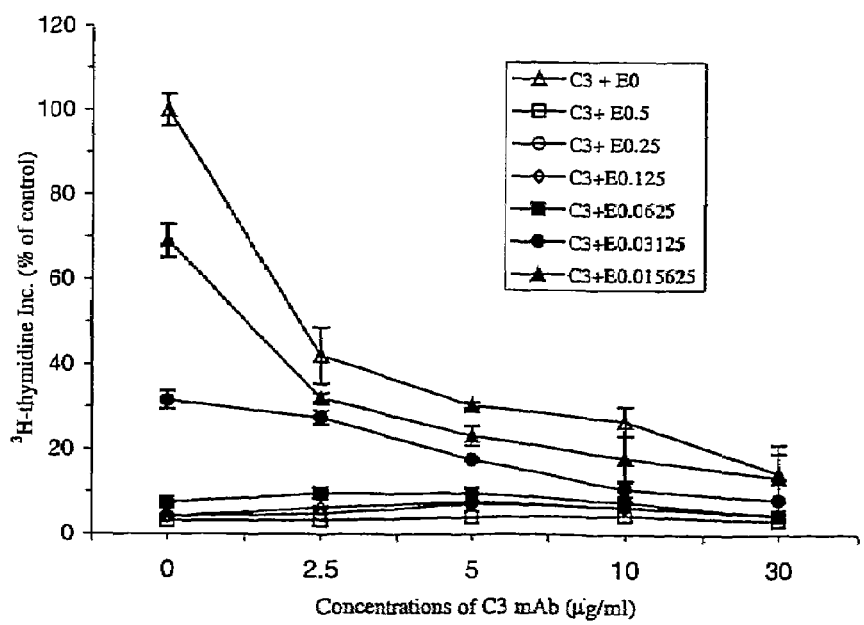

FIG. 13: Provides tabled and graphical results showing the effects of combining low concentrations of the anti-Cripto-1 Mab, C3 and cisplatin on the growth of the prostate cancer cell line, PC3.

Figure 14:
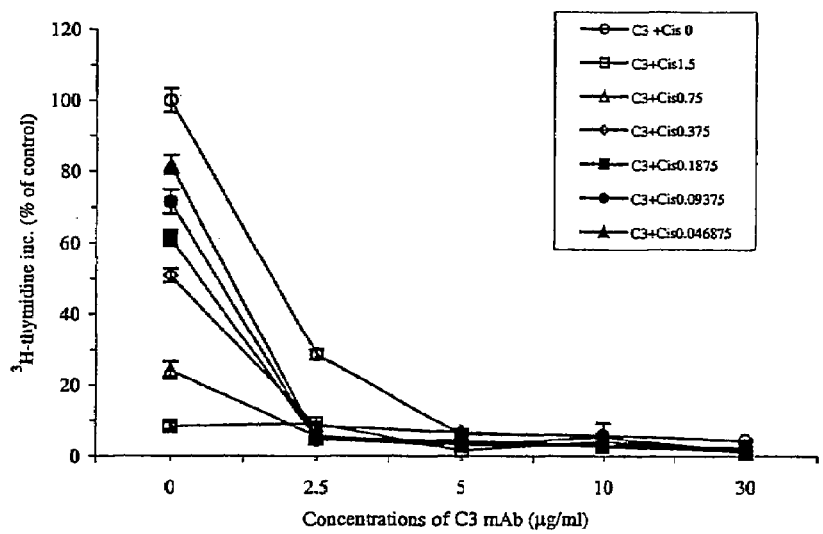

FIG. 14: Shows the effects of combining low concentrations of the anti-Cripto-1 Mab, C3 and Cisplatin on the growth of the prostate cancer cell line, DU 145.

Figure 15:
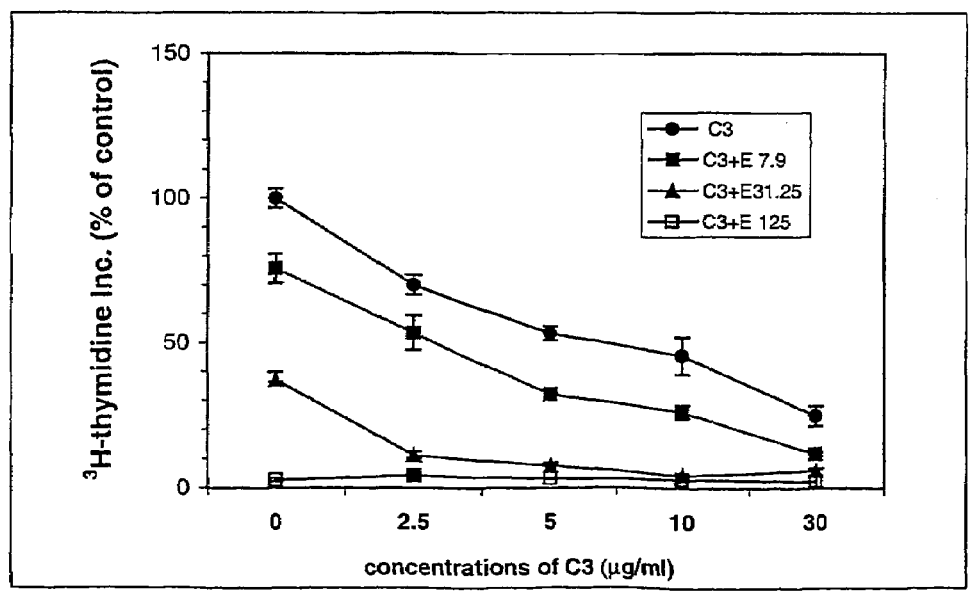

FIG. 15: Provides graphical results which show the inhibition of LS174T cell growth by Mab C3 and Epirubicin (7.9-125 µg/ml).

Figure 16:
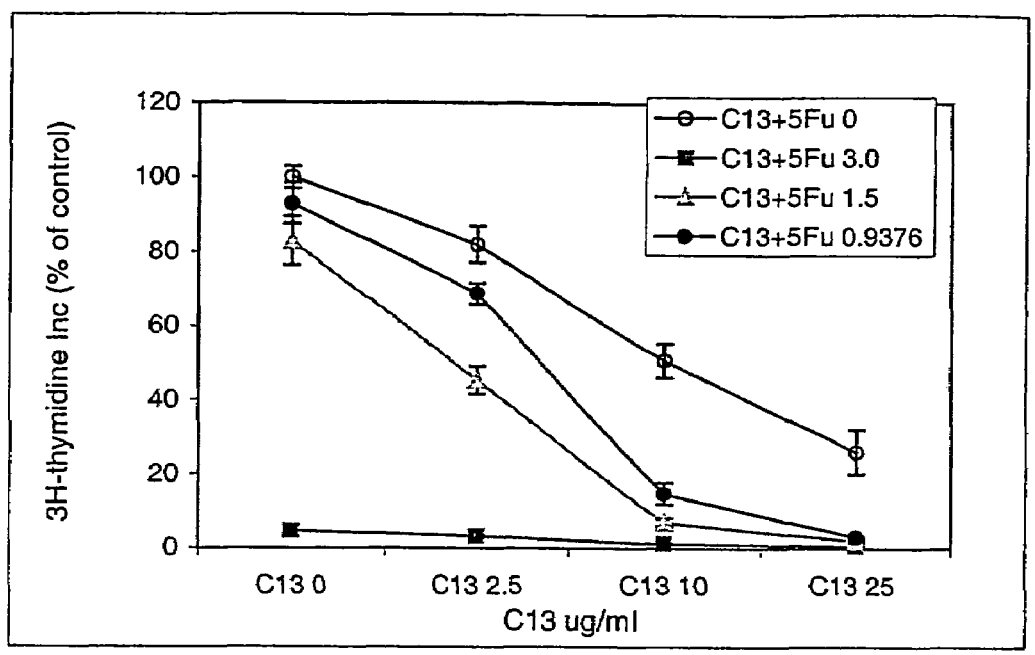

FIG. 16: Provides graphical results which show the inhibition of LS174T cell growth by Mab C13 and 5FU (0-3.0 µg/ml).

Figure 17:
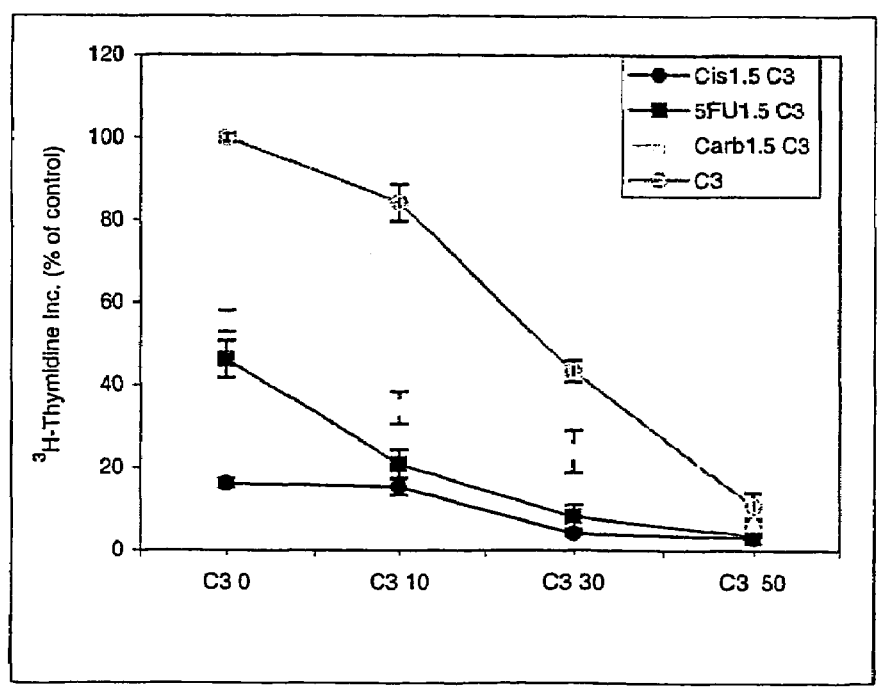

FIG. 17: Provides graphical results showing inhibition of growth of the breast cancer cell line MCF7 (ATCC, USA) by the anti-Cripto-1 Mab, C3 alone, or when combined with the cytotoxic drugs cisplatin (Cis), 5-Fluoricil (5FU) or carboplatin (Carb) (David Bull Laboratories, USA).

Figure 18:
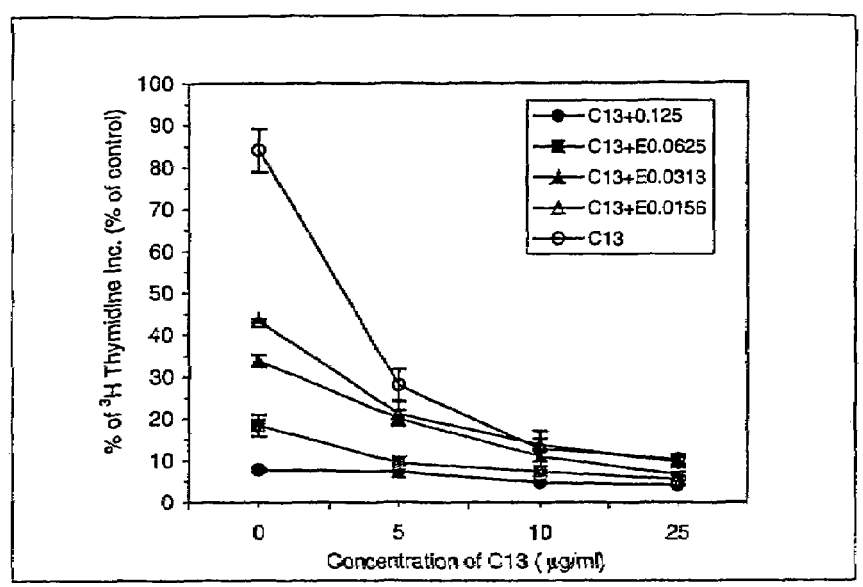

FIG. 18: Shows the inhibitory effect of Mab C13 and Epirubicin (E) on breast cancer cell MCF-7.

Figure 19:
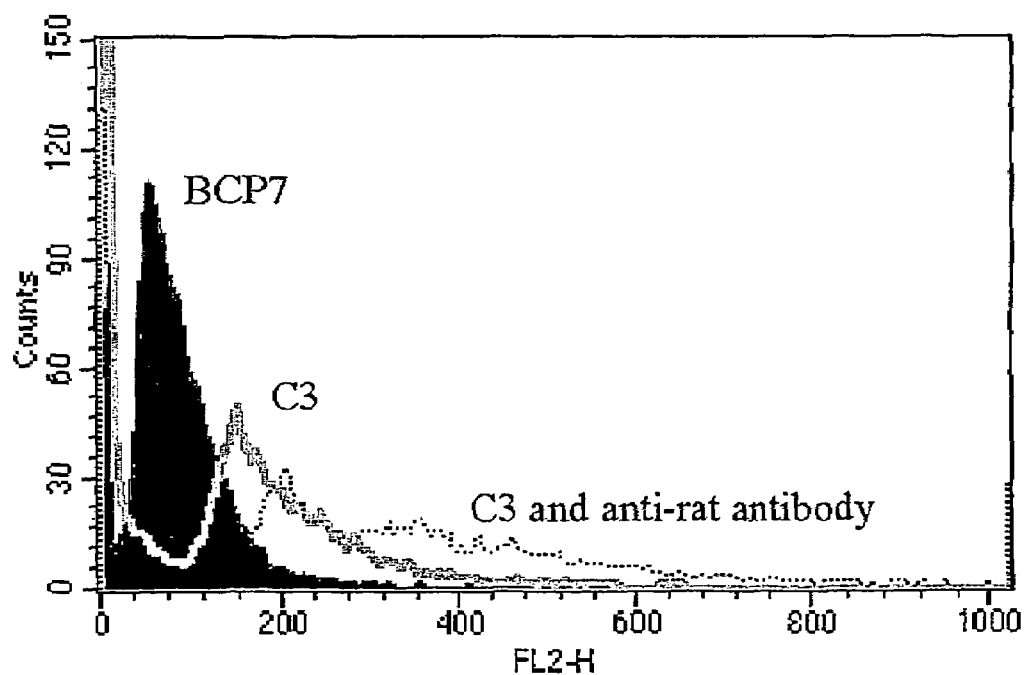

FIG. 19: Provides graphical results showing the inhibitory effect of cross-linked Mab C3 on the breast cancer cell line MCF7.

Figure 20A:
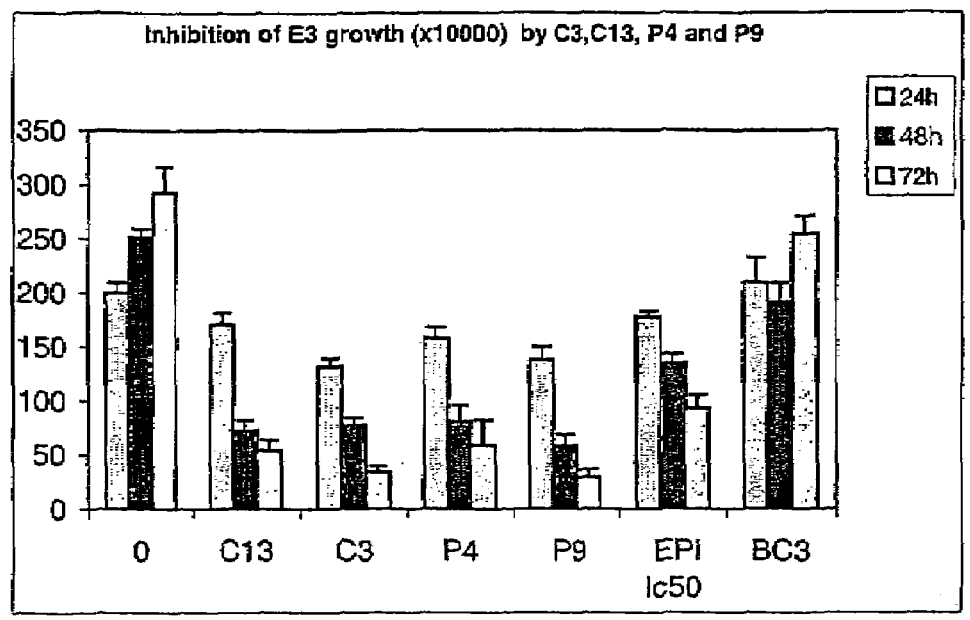
Figure 20B:
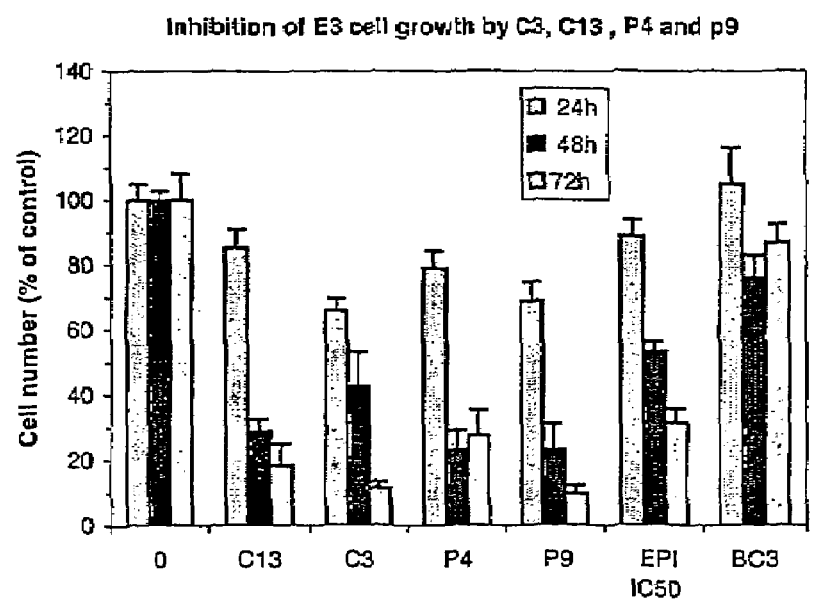

FIG. 20: Provides graphical results from incubation of mouse thyoma E3 cells (Austin Research Institute, Heidelberg, Victoria, Australia) in the presence of anti-Cripto-1 Mabs C3 and C13 and the anti-Pim-1 Mabs P4 and P9 for 24 to 72 hours, showing a reduction in cell numbers compared with cells which have not been exposed to the Mabs, control antibody BC3, an anti-Mucin 1 antibody (Austin Research Institute, Heidelberg, Victoria, Australia) and the drug Epirubicin (David Bull Laboratories, USA) at an Ic50 concentration of 20 ng (A). FIG. 20(B) provides graphical results from the same experimentation presented in FIG. 20(A), but in this case shows the inhibition of cell growth as a percentage of the control in which no Mabs are present.

Figure 21:
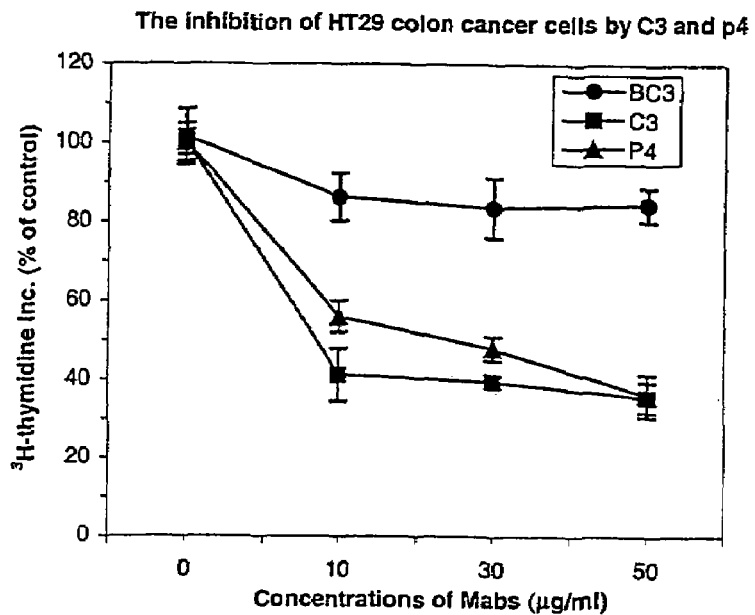

FIG. 21: Provides graphical results which shows inhibition of growth of the colon cancer cell line HT 29 (ATCC, USA) by the anti-Cripto-1 Mab, C3 and the anti-Pim-1 Mab, P4 compared with control antibody BC3.

Figure 22:
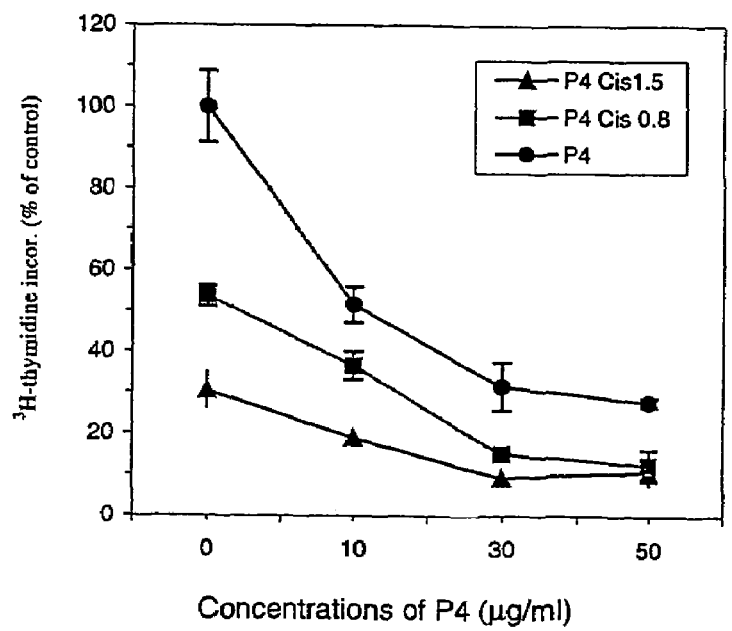

FIG. 22: Provides graphical results which show the inhibition of growth of the colon cancer cell line LS174T by anti-Pim-1 Mab, P4 either alone, or combined with increasing concentrations of Cisplatin.

Figure 23:
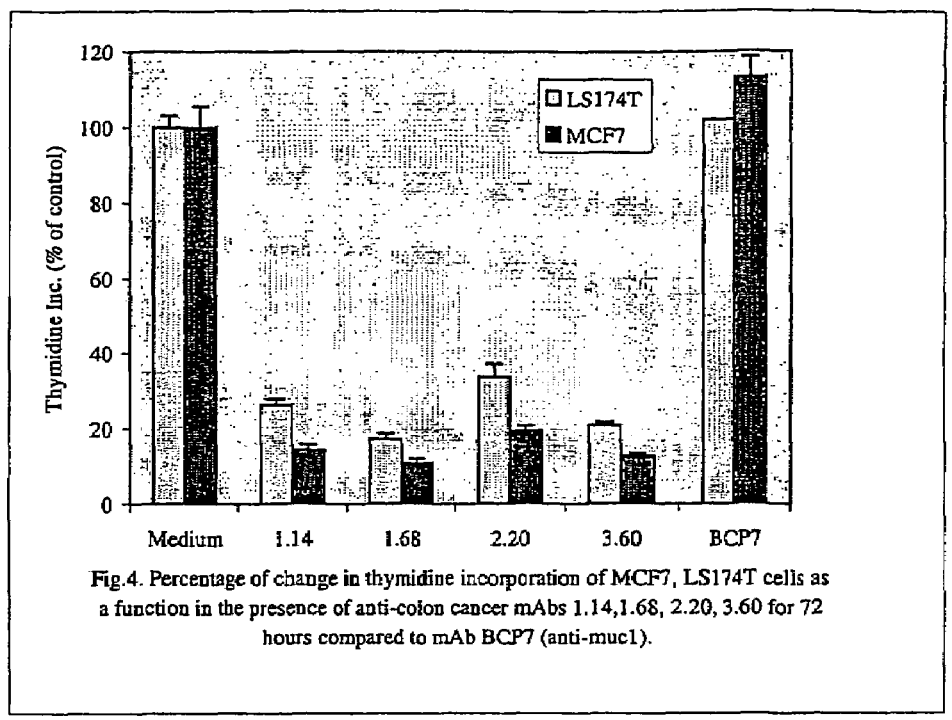

FIG. 23: Provides graphical results showing, by way of percentage change in $^3$H-thymidine incorporation, the inhibition of growth of the colon cancer cell line LS174T (ATCC, USA) and breast cancer cell line MCF7 by Mabs 1.14, 1.68, 2.20 and 3.60, using anti-Mucin 1 antibody BCP7 as a control.

Figure 24:
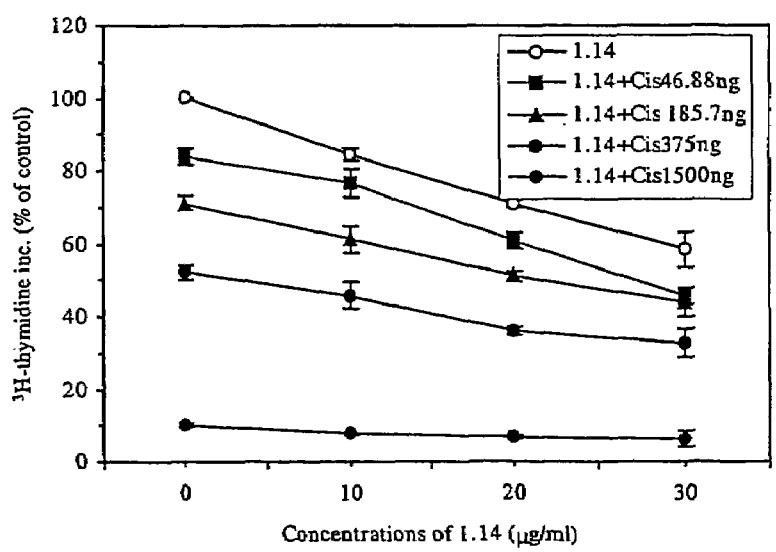

FIG. 24: Shows the effects of combining Mab 1.14 (raised against a colon cancer cell lysate) and Cisplatin on growth of the prostate cancer cell line, DU 145.

Figure 25:
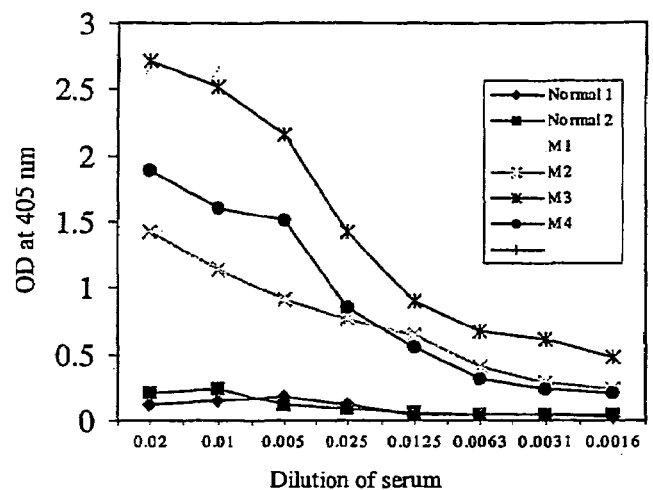

FIG. 25: Shows the results of titrations of mouse serum tested by ELISA using 37-mer Cripto-1 peptide coated plates.

Figure 26:
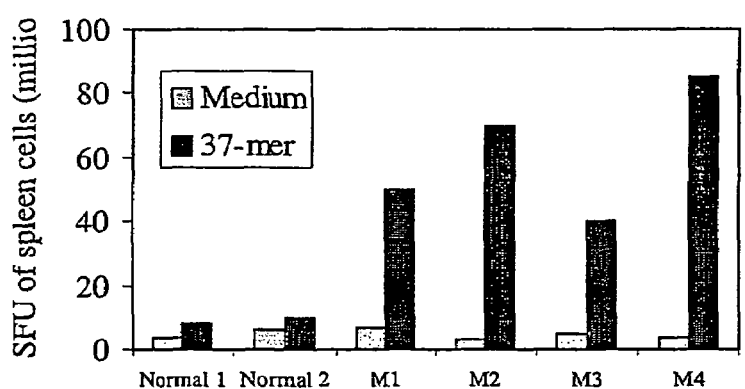

FIG. 26: Shows the results ELISPOT assays for IFNγ secretion. Mouse spleen cells from immunised and naive mice (normal 1 and 2) were stimulated overnight with and without the 37-mer peptide, and spot forming units (SFU) were counted by dissection microscope.

Figure 27:
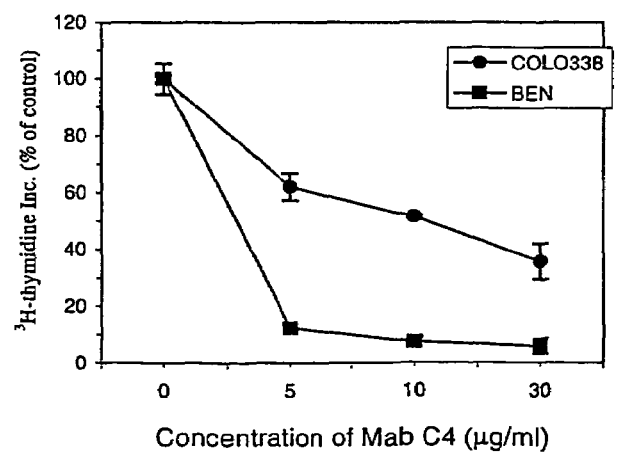

FIG. 27: Shows the percentage change in $^3$H-thymidine incorporation of lung cancer Ben and Colo 338 cells as a function of increasing concentrations of Mab C4 cultured for 72 hours, showing 90% and 60% inhibition in Ben and Colo338 cells respectively induced by Mab C4. Points, mean of triplicate experiments, bars, SD.

EXAMPLES

Introduction

In colon cancer, there is no response to radiotherapy and little response to drugs such as 5FUDR, levamasole, although recently there has been some improvement with the topoisomerase inhibitor Irinotecan. The prognosis for colon cancer patients in advanced disease (i.e. Dukes B, C, D) where there is local spread through nodes to distant metastases (Dukes D) is poor; in Dukes D few patients survive a year after diagnosis.

For breast cancer, the prognosis is considerably better, other than for those patients with primary disease, and a number of patients do well with cytotoxic/hormonal and radiotherapy treatment. Where the breast cancer is HER-2/neu positive (as it is in approximately 30% of patients), a proportion of patients respond well to the HER-2/neu Mab mentioned above.

There is a continuing need to identify and develop new treatments for colon and breast cancers.

Production of Antibodies (1) Lewis rats were immunised in accordance with standard techniques in the art with a KLH-coupled, 17 amino acid peptide derived from Cripto-1 protein having the sequence; CPPSFYGRNCEHDVRKE (SEQ ID NO:1). This sequence corresponds to residues 97-113 of the human and mouse Cripto-1 protein. It forms part of a modified EGF-like motif that differentiates Cripto-1 from other members of the EGF family (Brandt R, et al. "Identification and biological characterization of an epidermal growth factor-related protein: cripto-1", J Biol Chem, 269, pp 17320-17328 (1994); Salomon D. S. "Cripto: a novel epidermal growth factor (EGF)-related peptide in mammary gland development and neoplasia", Bioassays, 21, pp 61-70 (1999)).

(2) Balb C mice were immunised in accordance with standard techniques with a colon cell lysate prepared by freeze-drying tumour tissue followed by thawing, *repeated three times. The freeze/thaw samples were then homogenised three times for one minute each in phosphate buffered saline containing protease inhibitor.

(3) Balb C mice were immunised in accordance with standard techniques with a 59 kD fusion protein of Pim-1 with glutathione-S-transferase (GST) (provided by Dr Nancy S Magnuson, Department of Microbiology, Washington State University, USA).

Spleen cells from the immunised rats were isolated and fused with the myeloma NS1 (Xing PX, etal. "Monoclonal antibodies to mucin VNTR peptides", Methods Mol Biol, 125, pp 369-381 (2000)) cells to produce antibody-secreting hybridomas. Hybridomas were initially screened by assessing the ability of antibody-containing supernatants to inhibit growth of cancer cell lines (ie colon cell lines LS174T and HT29, and breast cancer cell line MCF7) in vitro, using a simple assay involving growing LS174T and MCF7 cells ($1\times10^5$) in 25 cm$^2$ flasks (in 10 ml of medium) in the presence or absence of 50 µg/ml of anti-Cripto-1 Mabs (C3 and C13). Viable cells were counted by using a phase-contrast microscope on day 6 of the culture.

Assays for Inhibition of Cancer Cell Growth

Growth inhibition was also assessed by measuring inhibition of uptake of tritiated thymidine, counting cell numbers manually by a trypan blue exclusion assay or by using a colorimetric cytotoxidty assay SRB (sulforhodamine B) (Skehan P, "New calorimetric cytotoxicity assay for anti-cancer-drug screening", J Natl Cancer Inst. 82, pp 1107-1112 (1990)) which is a rapid and sensitive method for measuring the cellular protein content of the cells.

EXAMPLE 1

Isolation of Anti-Cripto-1 Antibodies and Summary of Experimental Results

Two of the isolated Mabs (ie C3 and C13) bind to Cripto-1 (a member of EGF family encoded by CR1 in humans, tdgfl in mouse), a soluble or, possibly, cell surface (Mr 36 Kd) GPI-linked protein that appears to be a growth factor which promotes cell survival and proliferation and is important in embryonic development and cancer (Brandt R, supra) which has been described in a number of species (eg xenopus, zebrafish, mouse and human). Importantly, in the context of the present invention, the expression of Cripto-1 is increased several fold in human colon, gastric, pancreatic, breast and lung cancers and this increase can be detected in premalignant lesions (Brandt R, supra; Saeki T. et al. "Differential immunohistochemical detection of amphiregulin and cripto in human normal colon and colorectal tumours", Cancer Res, 52, pp 3467-3473 (1992); Salomon D S, supra; Panico L. et al. "Differential immunohistochemical detection of transforming growth factor alpha, amphireguliln and CRIPTO in human normal and malignant tissues", Int J Cancer, 65, pp 51-56 (1996)). For example, normal colon and breast cells do not contain Cripto-1, whereas it is found in ~85% of colon and breast cancers.

These anti-Cripto-1 Mabs have yet to be fully characterised with regard to the distribution of tissues to which they bind (especially in developing human mammary gland, lactation and during pregnancy), but using immnunoperoxidase staining with fresh or formalin fixed human tissue, indicates that the Mabs are cancer specific and bind to an antigen present in colon cancer (60%) and breast cancer (70%) but which is absent from normal colon tissue. In addition, the present applicants have observed that the anti-Cripto-1 Mabs react with mouse tumours. More importantly, these antibodies showed significant inhibition of the growth of the colon cancer cell line LS174T and breast cancer cell line MCF7 in tissue culture. In addition, these Mabs also showed inhibition of leukemia, lung cancer cells and prostate cancer cells.

In other experimentation, it has been found that by cross linking the antibodies in vitro with a secondary anti-rat antibody an increase in apoptosis can be achieved. Dose response trials have also been conducted in vitro with cytotoxic compounds including 5FU, Cisplatin and Carboplatin, which showed that substantial increases in the level of inhibition of cancer cell division and growth may be achieved when the Mabs are used in combination with cytotoxic compounds, but also there is a real decrease in cell numbers, indicating that the Mabs induced cancer cell apoptosis.

EXAMPLE 2

Monoclonal Antibody C4 to Cripto-1

A further anti-Cripto-1 monoclonal antibody, Mab C4 was obtained using the same method as used to raise Mabs C3 and C13. Each Cripto-1 Mab was selected by a) detection of immnunoperoxidase staining to determine binding of the antibody to a target tissue, b) cell growth inhibition assay eg $^3$H-thyrnidine assay in a selected cell line (antibodies showing >60% inhibition by thymidine incorporation) and c) detection of 2-fold decrease in cell no. as determined by trypan blue exclusion. The top line in FIG. 1 shows the inhibition of the LS174T colon cancer cell line by Mab C4 after 72 h of co-culture, whilst FIG. 2 shows the reduction in cell count number by the Mabs C4, C3 and C13 after 7 days of culturing 1×10$^4$ of the cells in 25 cm$^2$ flasks in 10 ml of medium with 30 µg/ml of each Mab. The antibody also enhanced the sensitivity of LS174T to Cisplatin in that addition of the Mab to cells being treated with the drug reduced $^3$H-thymidine incorporation further relative to incubation with the drug alone at 0.0938 to 0.75 µg/ml.

Similar results were obtained with Epirubicin and 5FU. After 72 h incubation with 0, 10, 20 and 30 µg/ml Mab C4, tritiated thymidine incorporation by LS174T cells was inhibited by 50 to 90% in the presence of 0.04, 0.08, 0.1625 and 0.125 µg/ml Epirubicin. For 5FU, thymidine incorporation was inhibited by 50 to 90% in the presence of 1.5, 1.9, 2.1 and 2.4 µg/ml of the drug. 5FU is a mainstay of treatment for colorectal cancer and is an antimetabolite. The synergistic effect of combined use of 5FU, Cisplatin, Epirubicin will be clinically useful.

EXAMPLE 3

Testing of Binding of Anti-Cripto-1 Antibodies with Cancer and Normal Tissues

Figure 3A:
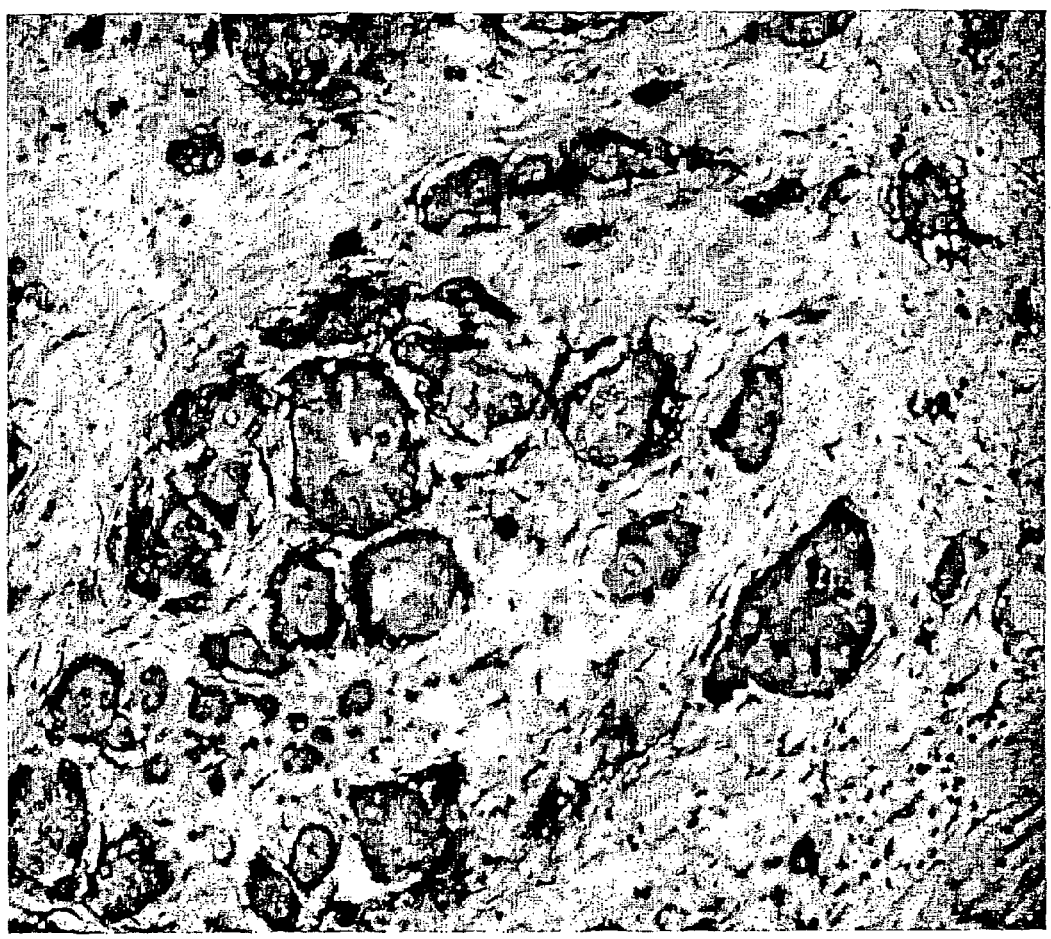
Figure 3B:
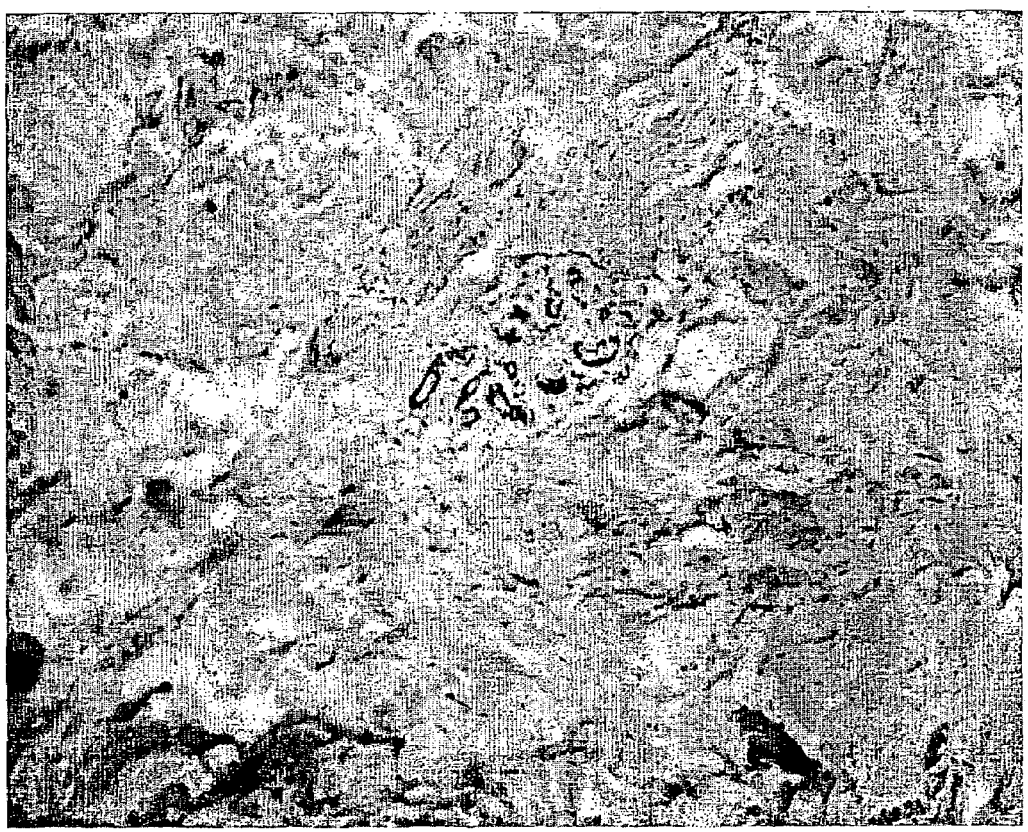

The anti-Cripto-1 Mabs reacted with a number of cancer cell lines, such as LS174T, HT29 (colon cancer), MCF7, T47D (breast cancer), DU145 and PC3 (prostate cancer), Ben and Colo 235 (lung cancer), but not with embryonal kidney cell line 293 when tested by FACS and immunoperoxidase staining. The 3 Mabs also reacted with formalin-fixed tissues, such as colon cancer (7/9), breast cancer (5/7), lung cancer of all types (18/20), stomach (3/4), pancreas (1/2), but did not react with normal breast (0/4), colon (0/8), lung (0/4), stomach (0/2), pancreas (0/2), liver (0/3), and lymphocytes (0/3) by immunoperoxidase staining. The intensity and percentage of staining varied from negative to very strong positive, indicating that Cripto-1 expression varies in different cancers. FIG. 3A shows immunoperoxidase staining breast cancer tissue by Mab C4, compared to FIG. 3B in which no staining of normal breast tissue by the antibody is observed.

EXAMPLE 4

In vivo Inhibitory Effect of Anti-Cripto-1 Antibodies on Growth of Colon and Prostate Cancer Cells in Mice SCID mice (6-8 week of age) were inoculated subcutaneously with 2×10$^6$ prostate cancer cell line DU145 at Day 0 and after 6 h the mice were treated with 500 µg of Mab C4 intraperitoneally, followed by 250 µg at days 2,4,7,9 and 10, and 125 µg at days 14 and 17. Phosphate buffered saline (PBS) (0.5 ml) was used as a control. Tumours were removed and measured at day 24. The tumour size and weight were significantly reduced by the treatment of Mab C4 (FIGS. 4A and 4B).

Similar results were also demonstrated in the colon cancer model (FIGS. 5A and 5B) using Mab C13, 500 µg after 16 h inoculation of LS174T cells, then 250 µg at days 2, 7,9, 11 and 13. Tumours were excised on day 25 for weight determination.

EXAMPLE 5

Apoptosis Induced by Anti-Cripto-1 Antibodies

The anti-Cripto-1 monoclonal antibodies stopped cell division as measured by a decrease in $^3$H-thymidine uptake, and decreased cell numbers (FIGS. 1 and 2 respectively), indicating that the Mabs induced cancer cell apoptosis. This was further demonstrated by DNA fragmentation and FACS assays (FIGS. 6 and 7).

In FIG. 6, soluble DNA was extracted from LS174T cells that had been treated for 72 hours with 50 µg/ml of Mab C3, and electrophoresed on 2% agarose gels. Control samples were from cells treated with cell culture medium.

FIG. 7 shows LS174T cells treated for 72 hours with 30 µg/ml Mab C4 or the control antibody Mab BCP7, then analysed by flow cytometry assay to determine propidiwA iodide (PI) staining, an indicator of apoptosis. The results showed an increase in PI staining in cells treated with the test Mab.

EXAMPLE 6

Signal Transduction Mediated by Anti-Cripto-1 Antibodies (i) Anti-Cripto-1 Mab Induced JNK Activation Signal transduction pathways controlled by protein kinase modules regulate critical cellular functions including cell growth, differentiation and apoptosis. Three major kinase cascades have been identified in control of apoptosis that culminate in the activation of three different sets of mitogen-activated protein kinases: the extracellular signal-regulated kinase (ERK), JNK/SAPK, and p38. ERK is activated by mitogens and survival factors, while JNK/SAPK and p38 are stimulated by stress signals. The stress-activated kinase cascades including the JNK/SAPK and the p38 pathways are activated in response to different apoptotic stimuli and seem to play a decisive role in apoptosis process.

The role of JNK and p38 activation in anti-Cripto-1 mediated apoptosis was investigated in colon cancer LS17T cell line using different concentration of Mabs and various times of incubation. In particular, JNK/SPAK was activated in LS174T cells following 3 hours incubation with anti-Cripto-1 Mab in a dose dependent manner (FIG. 8A). JNK activation was at the highest level after 24 hours of exposure (FIGS. 8B and 8D), and declined within 48 h, returning to basal level at 72 hours of incubation (FIG. 8D) indicating JNK activation by anti-Cripto1 antibodies is time dependent (ii) JNK Activation by Anti-Cripto-1 Antibodies Preceded p38 Activation The stress related p38 pathway was also investigated in LS174T cells following anti-Cripto-1 Mab treatment. p38 activation occurred following 48 hours of Mab exposure, when the level of activated JNK declined. p38 was further activated at 72 hours when elevated JNK returned to basal level (FIG. 8D). Thus, JNK activation occurred prior to apoptosis induced by Mab, whilst p38 was activated during the time when apoptosis occurs suggesting that both signals may be involved in the Mab induced apoptosis. In contrast, Cisplatin induced both JNK and p38 MAPK activation (FIGS. 8A and 8C), indicating that the Mabs activated JNK and p38 in a way different from Cisplatin. The potentiation of Cisplatin cytotoxicity by anti-Cripto-1 Mabs (FIG. 1) is accompanied by an increase in JNK phosphorylation (FIG. 8A) and p38 MAPK (FIG. 8B).

Thus, anti-Cripto-1 Mabs induce tumour cell apoptosis through activation of both JNK and p38.

(iii) ERK and Akt Phosphorylation and Cripto-1 Expression

The effect of Mab on the inhibition of ERK and Akt (FIGS. 8B and 8D) survival pathways has not been demonstrated. No changes in the levels of Cripto-1 expression were observed following Mab treatment (FIGS. 8B and 8D). These preliminary signalling studies clearly show that the anti-Cripto-1 Mabs cause apoptosis through the JNK activation pathway.

EXAMPLE 7

Inhibition of Leukaemia Cells by Anti-Cripto-1 Antibodies

FIG. 9 provides results showing that Mabs C3 and C13 inhibited growth of the T cell lymphoblastic leukaemia cell line CCRF-CEM. The antibodies also inhibited growth of the drug resistant variant of this cell line, CEM/A7R, which acquires this property by over-expression of P-glycoprotein. Thus, this cell line is normally resistant to a variety of naturally derived chemotherapeutic agents.

Figure 10A:
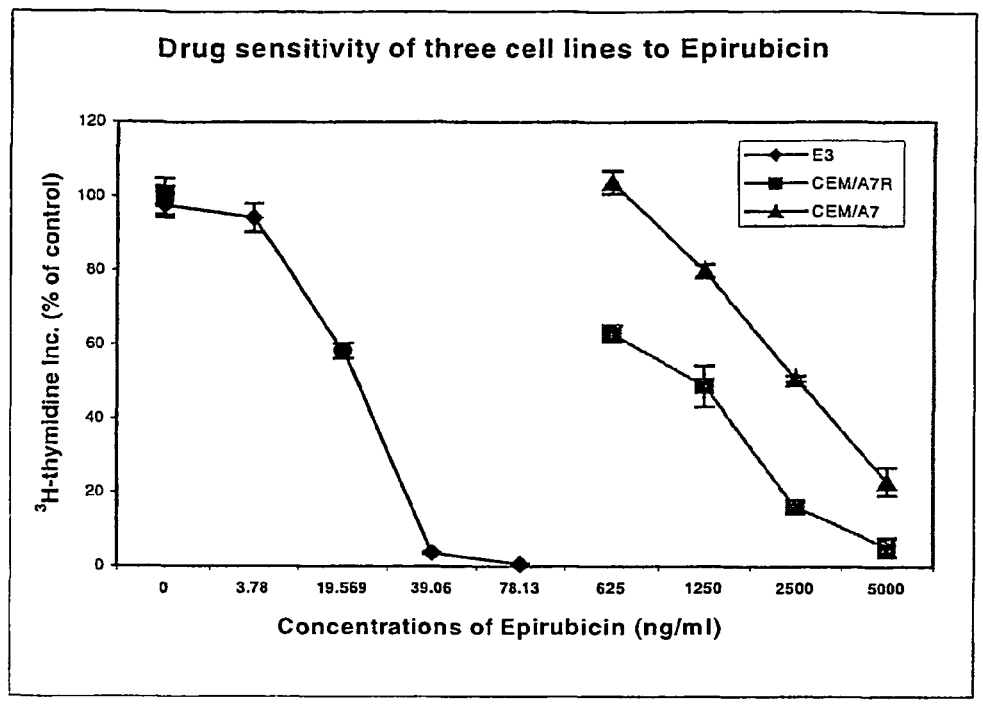
Figure 10B:
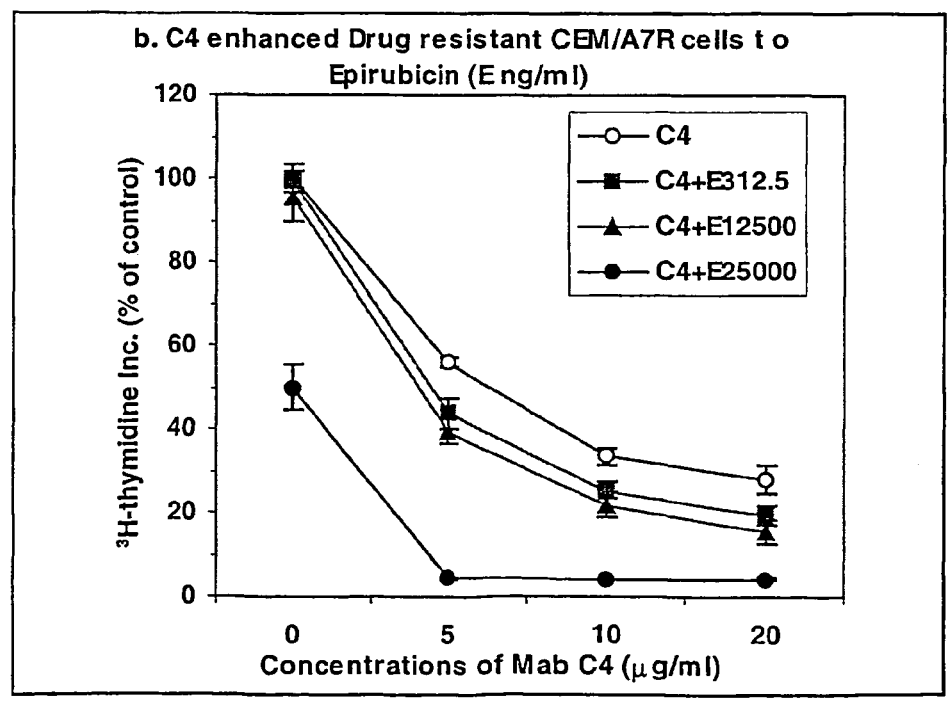
Figure 10C:
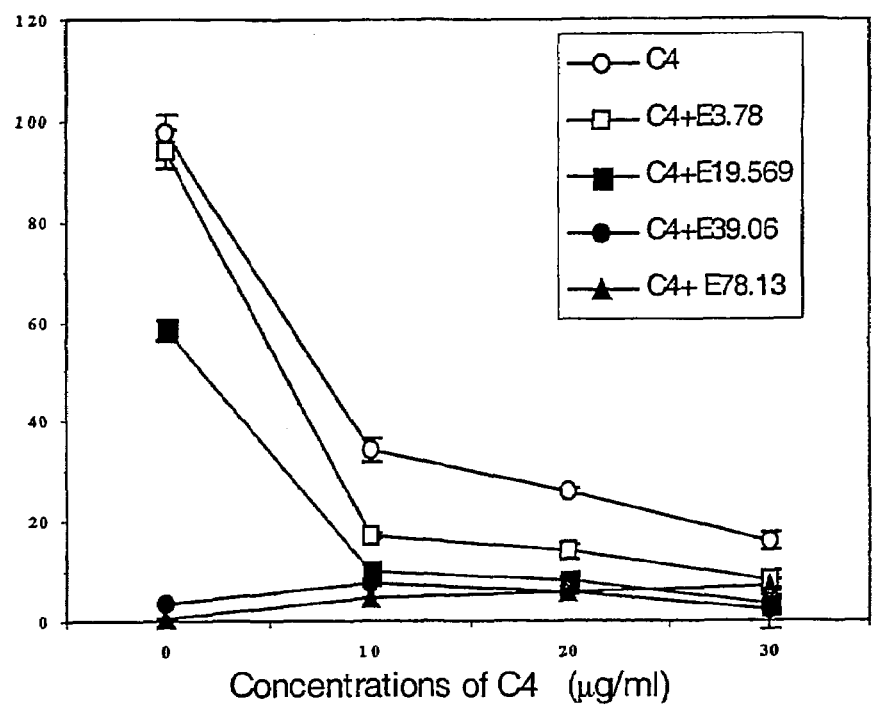

The Mab C4 showed a similar inhibitory effect on the drug resistant cell lines CEM/A7 and CEM/A7R and on a drug sensitive mouse thymoma cell line (ie E3). Compared to E3, CEM/A7 and CEM/A7R exhibit around 80 and 40 fold resistance to Epirubicin respectively (FIG. 10A). The antibody appears to sensitise the drug resistant cells (FIG. 10B) and drug sensitive cells (FIG. 10C) to Epirubicin. Therefore, C4 can overcome drug resistance which is a common problem in acute leukemia.

EXAMPLE 8

Effect of Anti-Cripto-1 Antibodies on Prostate Cancer

Cells from the prostate cancer cell line PC3 were cultured with 30 µg/ml Mab C3 for 6 days. Cell numbers were counted at days 2, 3 and 6. FIG. 11 shows that cell numbers were significantly decreased in the presence of the antibodies. Similar effects were also observed in drug resistant DU 145 cells, as shown in FIG. 12.

Mab C3 was also able to sensitise PC3 cells to the drug Epirubicin and DU 145 cells to the drug Cisplatin as shown in FIGS. 13 and 14 respectively.

EXAMPLE 9

Effects of Anti-Cripto-1 Antibodies and Anti-Cancer Drugs

The ability of Mab C4 to enhance the inhibitory effects of cytotoxic drugs such as Cisplatin in colon cancer cell LS174T is shown in Example 2 above. Similar effects were observed with Mab C3 and 13 with respect to Epirubicin and 5 FU respectively as shown in FIGS. 15 and 16.

EXAMPLE 10

Anti-Cripto-1 Antibodies and Breast Cancer

As shown in FIG. 17, Mab C3 inhibited growth of breast cancer cells MCF7, and further sensitised the cells to Cisplatin, Carboplatin and 5FU. Similar results were observed with Mab C13 and Epirubicin (FIG. 18).

EXAMPLE 11

Cross-linking of Anti-Cripto-1 Antibodies

Mab C3 was cross-linked by anti-rat antibody. The effect of cross-linking the Mab was investigated in breast cancer cell line MCF7, which was incubated with the antibody for 2 hours, and then incubated with rabbit-anti rat antibodies for 4 hours, followed by PI staining. BCP7 and MabC3 that had not been cross-linked were used as controls. FIG. 19 shows that cross-linking the Mab resulted in significantly more cell death as determined by flow cytometry using PI staining.

EXAMPLE 12

Isolation of Anti-Pim-1 Antibodies

Two isolated Mabs (ie P4 and P9) were raised against the product of the Pim-1 oncogene. This gene encodes a protein belonging to the ser-threonine kinase class of proteins. The anti-Pim-1 antibodies inhibited growth of mouse thyoma E3 cells (FIG. 20) and, along with the colon (FIGS. 21 and 22)

and breast cancer cell lines tested, these antibodies also showed inhibition of leukemia and prostate cancer cell lines (data not shown).

EXAMPLE 13

Isolation of Antibodies Against Colon Cell Lysate Antigens

Five of the isolated Mabs (ie 1.14, 1.68, 2.20, 3.60 and 4.57) were raised against unknown antigens by immunising rats with a lysate of fresh colon cancer tissue. These were also found to inhibit growth of the colon cancer cell line LS174T and breast cancer cell line MCF7 in tissue culture (FIG. 23). These antibodies also demonstrated inhibition of the prostate cancer cell line DU 145 especially when used in combination with Cisplatin (FIG. 24).

EXAMPLE 14

Humanisation of Antibodies

Fully human anti-Cripto-1 antibody are produced by using 2 peptides coupled to KLH as antigens for immunisation, namely the 17-mer (97-113) peptide (SEQ ID NO:1) used for the production of the Mabs C3, C4 and C13, and (2) a 37-mer peptide p47 (77-113) containing the 17-mer peptide and the putative binding site of Cripto-1 and its receptor (SEQ ID NO:2)
ELNRTCCLNGGTCMLGSFCACPPSFYGPNCEHDVRKE, and by testing these in vitro and in vivo in the same manner as that described above for the the production of rat-anti-Cripto-1 Mabs.

The antigens are used to immunise mice followed by cell fusions with the non-secreting myeloma cell line NSO-bcl 2 (which has no immunoglobulin gene) and screened, or otherwise are used to immunise a Human Ig mice (eg XenoMouse) wherein the mouse immunoglobulin genes have been "knocked out" and replaced by human genes such that they will only have human antibodies produced (nb multiple immunisations can be done and the mice screened for the presence of high affinity antibodies) followed by identification of B-cells that produce antibodies with inhibitory functional properties using microplate-based cell growth inhibition assay. The antibody encoding genes of individual B-cells producing inhibitory antibodies are then recovered and used to generate a panel of suitable recombinant candidate antibody products, each ready for manufacturing scale-up.

EXAMPLE 15

Clinical Uses of Antibodies

Human Mabs produced in accordance with the procedure described in Example 14 will be administered to patients by intravenous injection at a dose in the range of 0.5 mg-10 mg/kg body weight. The patients may also be administered with a suitable anti-cancer drug.

EXAMPLE 16

Effect of Cripto-1 Immunisation

In contrast to antibodies which are administered "passively" to the recipient, the Cripto protein or antigenic fragments thereof can be used to "actively" immunise, and produce a vaccine. In such a procedure, the Cripto antigen is combined with a carrier (eg alum, mannan, beads or other adjuvants) and used to immunise subjects with cancer as a preventative for cancer. The ensuing immune response can be:

a) generation of antibodies including but not limited to those described above;
b) production of T cells which recognise the Cripto antigen presented by MHC Class I or II molecules (the ensuing T cell response can be measured as effector cells as either: Cytotoxic T cells, Cytokine (eg interferon producing cells, such as ELISPOT or by other means), T cell proliferation, and/or delayed type hypersensitivity reaction in vivo); and/or
c) a combination of both antibodies and cellular immunity.

Thus Cripto-1 can be used to produce antibodies which are administered to the recipient or Cripto-1 can be used to "vaccinate" a patient who produces antibodies, T cells or both.

Mice were immunised using the Cripto-1 37-mer peptide mentioned above in Example 14 conjugated with KLH, which was emulsified with CFA. The immune responses were tested by ELISA and EUSPOT IFNγ assay. The mice responded in both antibody and INFγ productions (as shown in FIGS. 25 and 26).

EXAMPLE 17

Anti-Cripto-1 Antibodies and Lung Cancer

Mab C4 also inhibited, in a dose dependant manner, the incorporation of $^3$H-thymidine in lung cancer cells—Ben and Colo 38. In Ben cells, incorporation was inhibited by 90% after 72 h incubation with the Mab compared with control cells. In Colo 38 cells, the inhibition was 60% (FIG. 27).

Immunoperoxidase staining of the lung cancer cell line Ben or lung cancer tissues was also shown for Mab C3; both cell surface and cytoplasmic staining of lung cancer cells were observed, whereas no staining was seen in normal lung tissues.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of treating cancer in a subject having cancer cells that over-express Cripto-1 as compared to non-cancerous cells, comprising administering to said subject a therapeutically effective amount of a monoclonal antibody or fragment thereof that binds a Cripto-1, whereby growth or spread of cancer cells in the subject is inhibited and wherein the mechanism of inhibition of growth or spread of the cancer cells is through:
   (a) apoptosis induced by binding of the antibody or fragment thereof to the Cripto-1; or
   (b) cytotoxicity induced by delivery to cancer cells of a cytotoxic compound conjugated to said monoclonal antibody or fragment thereof.

2. The method of claim 1, wherein the monoclonal antibody or fragment thereof is a human monoclonal antibody or fragment thereof.

3. The method of claim 1, wherein the monoclonal antibody or fragment thereof is a chimeric monoclonal antibody or fragment thereof.

4. The method of claim 1, wherein the cancer is a colon cancer.

5. The method of claim 1, wherein the cancer is a breast cancer.

6. The method of claim 1, wherein the cancer is a prostate cancer.

7. The method of claim 1, wherein the cancer is a leukemia.

8. The method of claim 1, wherein the cancer is a lung cancer.

9. The method of claim 1, wherein the antibody or fragment thereof induces apoptosis of cancer cells.

10. The method of claim 9, wherein the antibody or fragment thereof induces apoptosis through activation of a JNK or p38 kinase cascade.

11. The method of claim 1, wherein the antibody or fragment thereof binds to an antigenic determinant of Cripto-1 protein comprising the amino acid sequence of SEQ ID NO: 1 or SEQ ID: 2.

12. The method of claim 1, wherein the mechanism of inhibition of grow or spread of cancer cells is apoptosis.

13. The method of claim 1, wherein the mechanism of inhibition of growth or spread of cancer cells is cytotoxicity.

14. The method of claim 13, wherein the antibody or fragment thereof is conjugated to a cytotoxic compound.

15. The method of claim 14, wherein the cytotoxic compound is selected from the group consisting of anthracyclines, 5-fluorouracil, topoisomerase inhibitors, cisplatin, carboplatin and taxol.

16. The method of claim 15, wherein the cytotoxic compound is an anthracycline selected from the group consisting of idarubicin, doxorubicin, daunorubicin and epirubicin.

17. The method of claim 16, wherein the cytotoxic compound is the topoisomerase inhibitor irinotecan.

* * * * *

SEQUENCE LISTING

<160> NUMBER OF SEQ ID NOS: 2

<210> SEQ ID NO 1
<211> LENGTH: 17

```
<212> TYPE: PRT
<213> ORGANISM: Homo sapiens

<400> SEQUENCE: 1

Cys Pro Pro Ser Phe Tyr Gly Arg Asn Cys Glu His Asp Val Arg Lys
1               5                   10                  15

Glu

<210> SEQ ID NO 2
<211> LENGTH: 37
<212> TYPE: PRT
<213> ORGANISM: Homo sapiens

<400> SEQUENCE: 2

Glu Leu Asn Arg Thr Cys Cys Leu Asn Gly Gly Thr Cys Met Leu Gly
1               5                   10                  15

Ser Phe Cys Ala Cys Pro Pro Ser Phe Tyr Gly Pro Asn Cys Glu His
            20                  25                  30

Asp Val Arg Lys Glu
            35
```